United States Patent [19]
Brantly et al.

[11] Patent Number: 5,439,824
[45] Date of Patent: Aug. 8, 1995

[54] INCREASED EXPRESSION OF α-1-ANTITRYPSIN IN EXPRESSION VECTORS THROUGH THE INCLUSION OF INTRON II

[75] Inventors: Mark Brantly, Silver Spring; Victor Laubach, Bethesda, both of Md.

[73] Assignee: The United States of America, Washington, D.C.

[21] Appl. No.: 60,925

[22] Filed: May 6, 1993

[51] Int. Cl.$^6$ ............ C12N 15/11; C12N 15/12; C12N 15/63; C12P 21/00
[52] U.S. Cl. .................. 435/320.1; 536/23.5; 536/24.1; 435/69.2; 435/172.3
[58] Field of Search .............. 536/23.5; 535/320.1, 535/91.4

[56] References Cited

U.S. PATENT DOCUMENTS 4,752,576  6/1988  Brake et al. ............ 435/69.2
5,108,909  4/1992  Haigwood ............... 435/692

FOREIGN PATENT DOCUMENTS 9005188  5/1990  WIPO .

OTHER PUBLICATIONS

Ragg et al., J. Biol. Chem. 263:12129–12134 (1988).
Reid et al., Proc. Natl. Acad. Sci. USA 87:4299–4303 (1990).
Satoh et al., Am. J. Hum. Genet. 42:77–83 (1988).
Archibald et al., Proc. Natl. Acad. Sci. USA 87:5178–5182 (1990).
Whitelaw et al., Transgenic Res. 1:3–13 (1991).
Buchman et al., Mol. Cell. Biol. 8:4395–4405 (1988).
Bao et al., Genomics; "Molecular Structure and Sequence Homology of a Gene Related to α1–Antitrypsin in the Human Genome"; 2:165–173.
Brinster et al., Proc. Natl. Acad. Sci. USA; "Introns Increase Transcriptional Efficiency in Transgenic Mice"; 85:836–840.
Chan et al., Gene; "Stability of Group I Intron RNA in Escherichia Coli and its Potential Application in a Novel Expression Vector"; 73:295–304.
Choi et al., Molecular and Cellular Biology; "A Generic Intron Increases Gene Expression in Transgenic Mice"; 11:3070–3074.
Crystal et al., Am. J. Med.; "Gene Therapy Strategies for Pulmonary Disease"; vol. 92 (Suppl 6A), pp. 44S–52S.
Dariavach et al., Eur. J. Immunol.; "The Mouse IgH 3'-Enhancer"; 21:1499–1504.
Hofker et al., Hum. Genet.; "a Pro Leu Substitution in Codon 369 of the α–1–Antitrypsin Deficiency Variant PI MHeerlen"; 81:264–268.
Jonsson et al., Nucleic Acids Research; "Intron Requirement for Expression of the Human Purine Nucleoside Phosphorylase Gene"; 20:3191–3198.
Ledley et al., Pediatric Research ; "Development of a Clinical Protocol for Hepatic Gene Transfer: Lessons Learned in Preclinical Studies"; 33:313–320.
Lemarchand et al., Proc. Natl. Acad. Sci. USA; "Adenovirus-Mediated Transfer of a Recombinant Human α1–Antitrypsin cDNA to Human Endothelial Cells"; 89:6482–6486.
Liu et al., Fed. Proc.; 69th Annual Meeting of the Federation of American Society for Experimental Biology; 44(5): 1613 (1985).
Long et al., Fed. Proc. Fed. Am. Soc. Exp. Biol.; "DNA Sequence of the Human α-1–Antitrypsin Gene" 42(7):1761 (1983).
Maas et al., Plant Molecular Biology; "The Combination (List continued on next page.)

Primary Examiner—Robert A. Wax
Assistant Examiner—Eric Grimes
Attorney, Agent, or Firm—Knobbe Mattens Olson & Bear

[57] ABSTRACT

The present invention relates to novel expression vectors and a method to increase the expression of $\alpha_1$-antitrypsin (AAT) from expression vectors encoding for the same through the inclusion of the Intron II sequence. Preferably, the Intron II sequence is included in its naturally occurring position, immediately after Exon II. Also, the invention is methods of therapy using the method and the expression vectors.

8 Claims, 13 Drawing Sheets

OTHER PUBLICATIONS of a Novel Stimulatory Element in the First Exon of the Maize Shrunken-1 Gene with the Following Intron 1 Inhances Reporter Gene Expression up to 1000-Fold"; 16:199-207.

Mascarenhas et al., *Plant Molecular Biology;* "Intron-Mediated Enhancement of Heterologous Gene Expression in Maize"; 15:913-920.

Matsunaga et al., *Am. J. Hum. Genet.;* "Molecular Analysis of the Gene of the $\alpha_1$-Antitrypsin Deficiency Variant, Mnichinan"; 46:602-612.

Olsen et al., *FEBS Letters;* "Cloning of the Pig Aminopeptidase N Gene"; 251:2575-281.

Oshima et al., *Genes & Development;* "Activation of an Intron Enhancer within the Keratin 18 Gene by Expression of c-fos and c-jun in Undifferentiated F9 Embryonal Carcinoma Cells"; 4:835-848.

Perlino et al., *The EMBO Journal;* "The Human $\alpha_1$-Antitrypsin Gene is Transcribed from two Different Promoters in Macrophages and Hepatocytes" 6:2767-2771.

Prochownik et al., *J. Biol. Chemistry;* "Intron Structure of the Human Antithrombin III Gene Differs from That of Other Members of the Serine Protease Inhibitor Superfamily"; 260:9608-9612.

Tanaka et al., *Nucleic Acids Research;* "Enhancement of Foreign Gene Expression by a Dicot Intron in Rice but not in Tobacco is Correlated with an Increased Level of mRNA and an Efficient Splicing of the Intron"; 18:6767-6770.

Yoshimura et al., *Journal of Biological Chemistry;* "Adenovirus-Mediated Augmentation of Cell Transfection with Unmodified Plasmid Vectors"; 268:2300-2303.

INCREASED EXPRESSION OF α-1-ANTITRYPSIN IN EXPRESSION VECTORS THROUGH THE INCLUSION OF INTRON II

BACKGROUND OF THE INVENTION

1. Field of the Invention

The present invention relates to novel expression vectors and a method to increase the expression of $\alpha_1$-antitrypsin (AAT) from expression vectors encoding the same through the inclusion of the Intron II sequence.

2. Background of the Art

Alpha$_1$-antitrypsin (AAT) deficiency is one of the most common inherited disorders in the US, affecting an estimated 20,000–40,000 individuals. AAT is a relatively small plasma glycoprotein with 394 amino acids and three oligosaccharide sidechains. AAT is a member of the serine protease inhibitor superfamily. The serine protease inhibitor family consists of at least 12 genes, most of which are involved in the control of serine proteases in blood coagulation, in complement activation, and in certain aspects of inflammation reactions. The family members are believed to have evolved from a common ancestor gene over about 500 million years.

The gene that encodes AAT in the liver has been identified as a 10.2 kb gene, consisting of five exons, four of which together encode that protein, and four introns. Perlino et al. *EMBO J.* 6:2767–2771 (1987). The exons are separated by a series of introns or intervening sequences.

There are two categories of AAT defects that cause disease states. The first category includes the deficient allele, in which AAT is present in low levels in the blood serum. The second category is the null alleles, in which no AAT in the blood serum can be detected.

AAT is synthesized primarily in the liver and subsequently secreted into the bloodstream where it serves as the predominant serine protease inhibitor. Although AAT is capable of inhibiting a variety of proteases including trypsin, chymotrypsin, thrombin, kallikrein, and plasmin (Laurell et al. *The Plasma Proteins* Vol 1, pp. 229–264 (Academic Press, New York, (F. W. Putnam, Ed. 1975)), its major physiological role is to protect elastic tissues in the alveoli structure of the lung from hydrolysis by excessive neutrophil elastase.

Clinically, AAT is important in that its genetic deficiency predisposes individuals toward the development of pulmonary emphysema. However, it is also an important genetic disease in its manner of manifestation. In children, the deficiency is manifested as liver disease and leads to the second leading reason for liver transplants in children. In adults, the deficiency is manifested primarily in the lungs, with secondary manifestations in the liver. In the lungs, lack of AAT antiprotease activity from AAT deficiency results in the uncontrolled breakdown of alveolar connective tissue leading to emphysema (Gadek et al. *The Metabolic Basis of Inherited Disease* pp. 1450–1467 (5th edition, McGraw-Hill, New York (1982)). For this reason, inheritance of two deficient AAT alleles substantially increases an individual's risk of developing emphysema or liver disease.

Accordingly, many investigators have been studying the gene regulation of AAT in an attempt to determine methods of treating individuals having the gene deficiency.

For example, Long et al. *Fed. Proc. Fed. Am. Soc. Exp. Biol.* 42(7):1761 (1983) disclosed the DNA sequence of the α1-antitrypsin gene and studied the structure of a large intron corresponding to the 5′ untranslated portion of the mRNA. Matsunaga et al. *Am. J. Hum. Genet.* 46(3):602–612 (1990) disclosed the sequence of $\alpha_1$-antitrypsin mutants as compared with normal $\alpha_1$-antitrypsin gene sequences. Their results revealed that there were differences between the intron sequences of the mutant and wild-type genes, although these differences did not result in different gene splicing patterns.

PCT Publication No. 90/05188 to Archibald et al. disclosed a method for producing large amounts of a medically important human proteins in the milk of transgenic animals by producing a construct encoding the medically important protein that contained an intron from that same protein. Archibald et al. incorporated DNA encoding for a heterologous protein together with at least one intron into a fusion protein that is a mammalian milk protein gene. The application indicated that, advantageously, high levels of protein expression were obtained from constructs employing some, but not all, naturally occurring introns in a gene.

Archibald et al. used α1-antitrypsin as one of its examples. In addition, the Archibald et al. application also cites a paper (Brinster et al., *Proc. Natl. Acad. Sci. (USA)* 5:836–840 (1988)), in which increased transcriptional efficiency is reportedly achieved by incorporating introns into transgenes in transgenic mice and that, importantly, introns from the native genome sequences yielded more efficient gene expression than foreign introns. However, Brinster et al. indicated that the effect is unique to transgenic animals and was not observed in cell lines. The Archibald et al. application goes on to cite the problems associated with manipulating large genome sequences containing all of the introns associated with a gene.

Others have also looked at introns as means for increasing gene expression. U.S. Pat. No. 5,108,909 to Haigwood discloses a method for improving expression of tissue plasminogen activator (tPA) in a mammalian cell by incorporating at least one tPA associated intron into an expression construct operably encoding tPA, where the intron is positioned in its native location.

Reid et al. *Proc. Natl. Acad. Sci. (USA)* 87(11):4299–4303 (1990) disclosed that hypoxanthine phosphoribosyltransferase (HPRT) required one HPRT intron for efficient cell expression. The intron's presence was not required for splicing and was not associated with a traditional transcription enhancer element that had been identified in another HPRT intron. While Brintner et al. (supra) limited the observation to transgenic animals, Reid et al., demonstrated the effect in somatic cells.

Jonsson et al. *Nucl. Acids Res.* 20(12):3191–3198 (1992) disclosed the addition of the first intron of purine-nucleoside orthophosphate ribosyltransferase (PNP) into a construct for PNP gene expression. They disclose the use of these PNP minigenes for retroviral-mediated gene transfer. Similarly, Chan et al. *Gene* 73(2):295–304 (1988) disclosed the use of *E. coli* intron sequences to increase the stability of chloramphenicol acetyl transferase (CAT) in bacteria.

Choi et al. *Mol. Cell. Biol.* 11(6):3070–74 (1991) disclosed using a heterologous intron consisting of an adenovirus splice donor and an immunoglobulin G splice acceptor to stimulate expression of CAT in a variety of tissues in a transgenic animal. Maas et al. *Plant. Mol.*

Biol. 16(2):199–207 (1991) and Mascarenhas et al. *Plant Mol. Biol.* 15(6):913–920 (1990) disclosed the enhanced expression of CAT in maize protoplasts by including introns from the maize alcohol dehydrogenase gene.

The above variety of intron effects on genomic expression of mRNA and protein demonstrate that the mode of action of introns in expression is not well understood. It is not until one or more introns are inserted and others are excluded from a vector and levels of expression measured, can one predict the effect that may be caused by the presence or absence of a particular intron.

Many disease states, such as those discussed above, might be treated by introduction of a gene encoding Alpha1-antitrypsin. Unfortunately, cloning of the complete gene is very difficult in retroviral or adenoviral shuttle vectors because of limitations in the size of insert DNA. In addition, gene expression with the $\alpha$1-antitrypsin cDNA has been found to be too low for use as a mechanism of treatment, regardless of the promoter used. It would provide a great advantage to have a gene that was capable of expressing high levels of AAT protein, but preferably, still be small enough to fit in a retroviral or adenoviral shuttle vector, i.e., less than or equal to 3000 bp in length.

SUMMARY OF THE INVENTION

In accordance with the present invention, there is provided an isolated DNA molecule encoding human $\alpha_1$-antitrypsin the molecule consisting essentially of DNA encoding the human $\alpha_1$-antitrypsin and intron II of the human $\alpha_1$-antitrypsin gene. Preferably, the isolated DNA molecule encoding human $\alpha_1$-antitrypsin comprises Exon II, Exon III, Exon IV and Exon V of the human $\alpha_1$-antitrypsin gene. In this embodiment, Intron II is preferably located between Exons II and III. Also, preferably, Exons IV and V follow Exon III.

In a preferred embodiment, the isolated DNA is in a vector, preferably an expression vector. In a highly preferred embodiment, the vector is pPI. In another embodiment, the vector is a viral vector.

In accordance with another aspect of the present of the present invention, a method to treat a mammal having a disease associated with $\alpha_1$-antitrypsin deficiency comprising administering to the mammal the isolated DNA described above, wherein the DNA is capable being expressed in the mammal. Preferably the administration is performed ex vivo. In such embodiment, the method advantageously comprising the additional step of reinfusing cells transfected ex vivo back into the patient.

The disease may be a genetic disorder where the gene encoding the production of $\alpha_1$-antitrypsin is absent from the patient. In the alternative, the disease may be a genetic disorder where the gene encoding the production of $\alpha_1$-antitrypsin is deficient in the patient. Or, the disease may be a genetic disorder that results in the degeneration of $\alpha_1$-antitrypsin in vivo. In a preferred embodiment, the disease is cystic fibrosis.

The vector used in the method may preferably be a plasmid. In the alternative, the vector may be a virus. In preferred embodiments, the virus is selected from the group consisting of a retrovirus and an adenovirus. In such embodiment the virus is advantageously administered to the cells of the patient in vivo. The method of administration of the virus to may be to the lungs of the patient through a method selected from the group consisting of inhalation and liquid lavage.

In accordance with another aspect of the present inveniton, there is provided a method of preparing a vector having enhanced expression of $\alpha_1$-antitrypsin, comprising constructing a DNA sequence operably encoding human $\alpha_1$-antitrypsin the molecule consisting essentially of DNA encoding the human $\alpha_1$-antitrypsin and Intron II of the human $\alpha_1$-antitrypsin gene. Preferably, the DNA encoding human $\alpha_1$-antitrypsin comprises Exon II, Exon III, Exon IV and Exon V of the human $\alpha_1$-antitrypsin gene.

BRIEF DESCRIPTION OF THE FIGURES

FIG. 9 are two diagrams showing the strategy of construction of AAT gene constructs that do not contain Intron II.

DETAILED DESCRIPTION OF THE PREFERRED EMBODIMENTS

Figure 1:
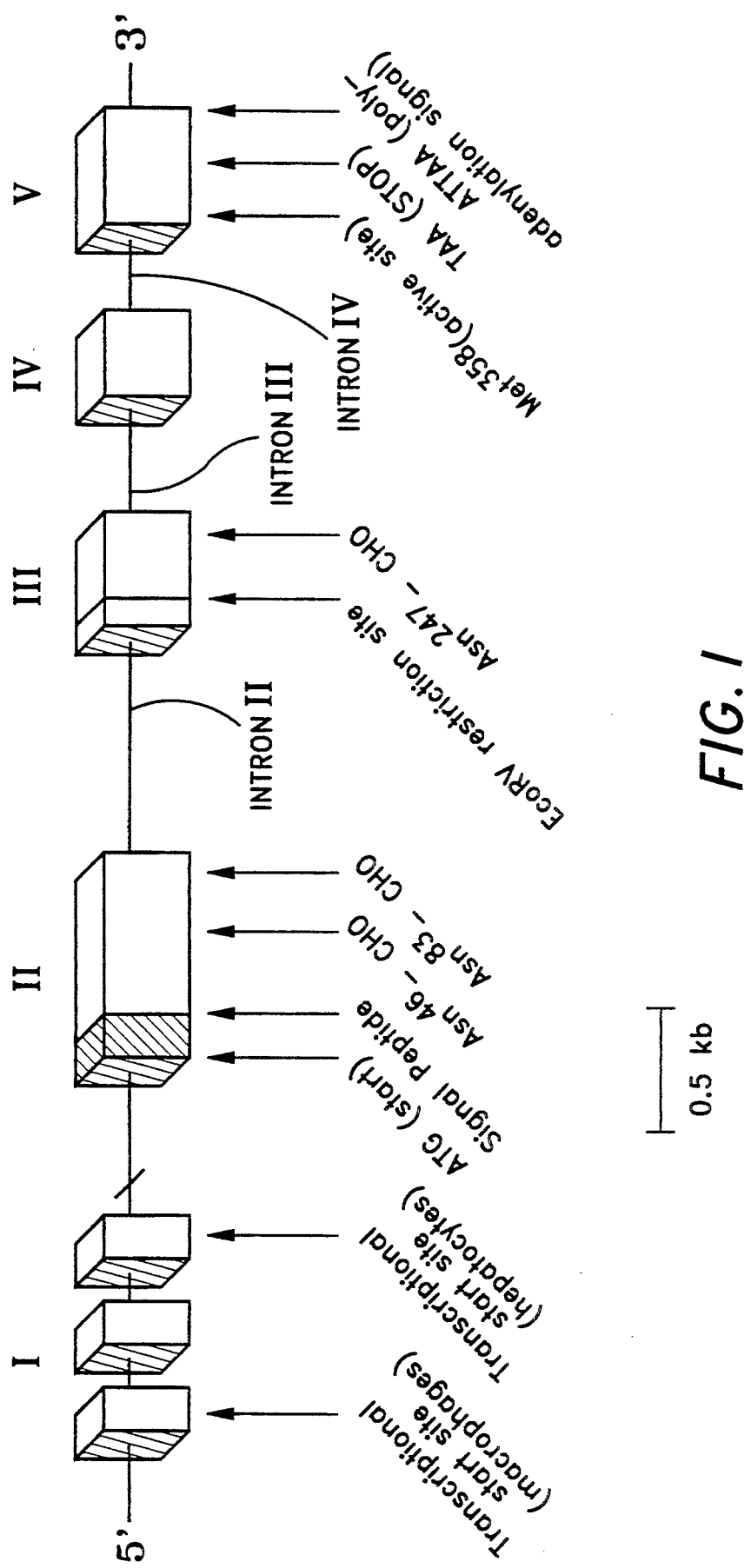
FIG. 1 is a schematic diagram of the sequence of the AAT gene and its genomic organization.

The present invention relates to the discovery that the inclusion of the Alpha$_1$-antitrypsin (AAT) Intron II, in its natural genomic position with respect to exons encoding sequences for AAT, markedly increases AAT gene expression. Gene expression of both mRNA and protein are increased by between 3 and 10 fold. Thus, the present invention solves a need for the high yield expression of AAT protein needed to provide effective therapy of diseases associated with the underexpression, absence, or overwhelming, of AAT.

In particular, we have also demonstrated that we can incorporate the AAT gene construct within a viral vector and the viral vector will enhance the levels of AAT secreted by cells. Our studies show that the AAT constructs of the present invention, when incorporated in a viral vector express AAT with greater efficiency than through the use of plasmid vectors. Thus, it is expected that viral vectors containing the AAT constructs of the present invention can be administered to a mammal and AAT will be expressed in high yields.

It is well established that one of the greatest challenges associated with finding therapies for patients having $\alpha_1$-antitrypsin deficiency (a disease that affects 40,000 Americans) is making sufficient amounts of $\alpha_1$-antitrypsin to correct the deficiency. Current $\alpha_1$-antitrypsin gene constructs produce much less $\alpha_1$-antitrypsin than what would be required to formulate a peptide-based treatment (Ledley et al. *Pediatric Research* 33:313–320 (1993)) the disclosure of which is hereby incorporated by reference. The gene construct of the present invention produces 3–10 fold more AAT than previous recombinant genes. Thus, the constructs of the present invention are an important advance in providing effective treatment for AAT deficient patients.

Viral vectors consisting of virus from both retroviral and adenoviral origin have been prepared and enhance AAT mRNA and protein expression in cells more than expression levels from the same viral vectors containing AAT cDNA without introns. Therefore, therapy of diseases associated with the underexpression or overwhelmance of AAT protein are clearly facilitated. It is well established that viral vectors will be taken up in and integrated into cells in vivo and express the viral DNA, including inserted constructs. See, e.g., Yoshimura et al. *J. Biol. Chem.* 268(4):2300–2303 (1993); Crystal *Am. J. Med.* 92(6A):445–525 (1992); Lemarchand et al. *Proc. Nat'l Acad. Sci. USA* 89(14):6482–6486 (1992) the disclosures of which are hereby incorporated by reference.

Thus, in accordance with the invention, adenoviral and retroviral facilitation of incorporation and therapy are contemplated. Also, adenoassociated viral vectors have shown great promise in therapeutic applications are also contemplated. Further, other delivery and incorporation aiding techniques are also suitable. Principally, these techniques include the use of liposomes and DNA conjugates are expected to provide similar delivery yields as those provided by the viral vectors discussed above. In addition combination therapies of adenoviruses and liposomes have also shown tremendous promise and are also contemplated for use in the invention. Yoshimura et al. *J. Biol. Chem.* 268(4):2300–2303 (1993) the disclosure of which is hereby incorporated by reference.

Referring now to FIG. 1, a schematic of the nucleotide sequence of AAT and its genomic organization is provided. In its natural state, the AAT gene consists of 3 noncoding Exons (Ia, Ib, and Ic), and four protein coding regions (Exons II–V). Between each of the Exons, there are intervening sequences (IVS) or introns. For example, between Exons II and III, an approximately 1500 bp intron (Intron II) resides. Exon II contains the first ATG start codon, while the TAA stop codon resides in Exon V. The full sequence of the $\alpha_1$-antitrypsin gene is disclosed in Matsunaga et al. *Am. J. Hum. Genet.* 46:602–612 (1990) the disclosure of which is hereby incorporated by reference. The $\alpha_1$-antitrypsin gene sequence is set forth in SEQ ID NO: 12. Exons II, III, IV and V correspond to nucleotides 5716-6364, 7816-8086, 9345-9492, and 10316-10583 of SEQ ID NO: 12, respectively. Introns II, III, and IV correspond to nucleotides 6365-7815, 8087-9344 and 9493-10315 of SEQ ID NO: 12, respectively.

Figure 2:
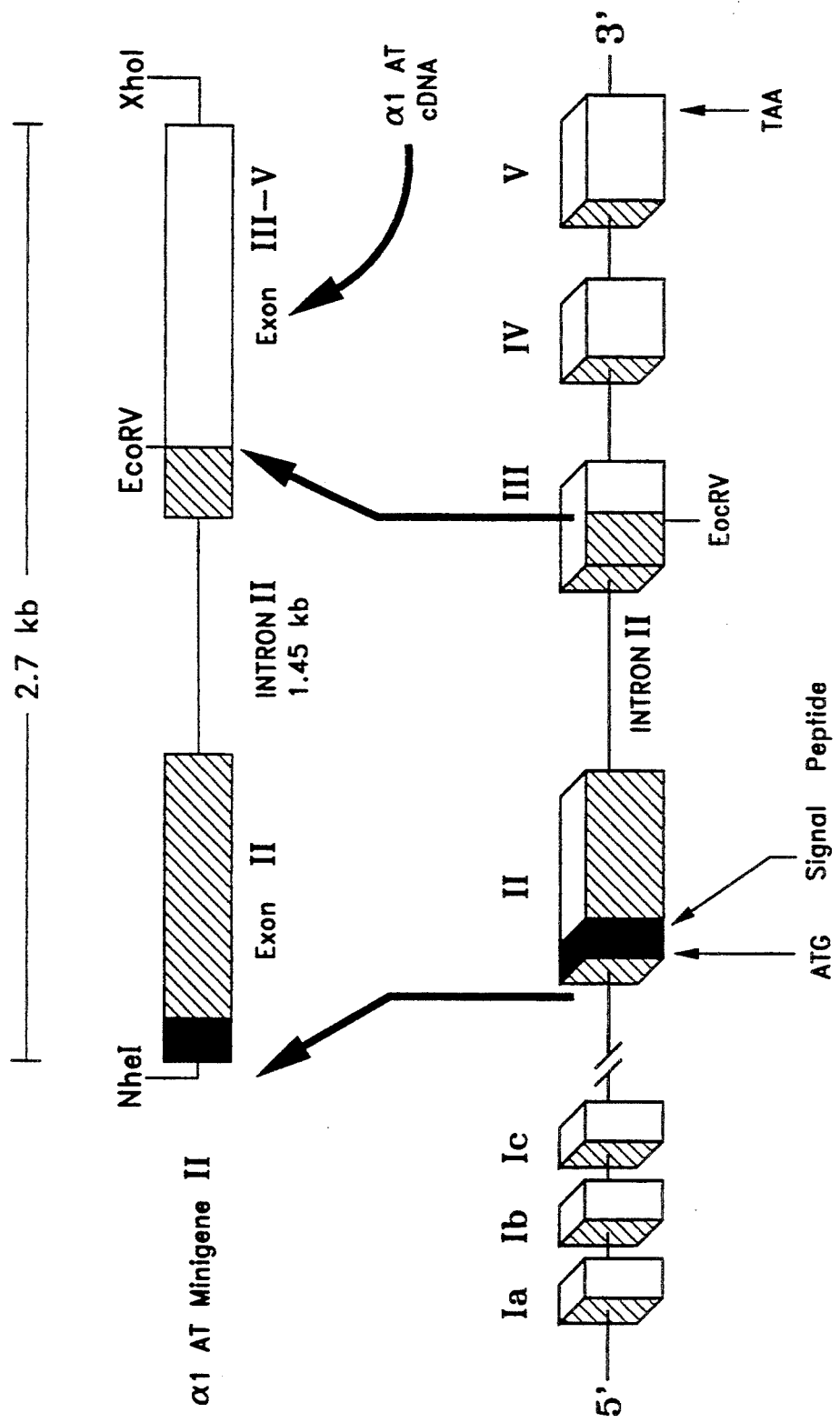
FIG. 2 is a schematic diagram of a preferred minigene prepared in accordance with the present invention that expresses 3–10 fold more AAT than AAT cDNA without Introns and AAT cDNA with Introns other than Intron II and the method of its preparation from the AAT gene and AAT cDNA.

In the present invention we have produced an expression plasmid, shown in FIG. 2 (top) that is derived from the AAT gene as shown in FIG. 2 (bottom) and FIG. 1. The construct has the 5' end of the first AAT coding sequence (Exon II) and the Exon II sequence operably linked to Intron II, in its naturally occurring position, in turn linked to the remaining coding regions, Exons III–V, without Introns III or IV. This construct will be referred to herein as MG 2 (with MG denoting minigene).

The inclusion of Intron II unexpectedly led to a 3–10 fold increase in AAT mRNA and protein production in comparison to cDNA clones not containing Intron II.

The MG 2 construct that we prepared has the additional advantage of being small enough to be successfully inserted into a viral vector and transcribed thereby. As will be understood, it is preferable that a construct be smaller than 3000 bp for effective incorporation into a viral vector. Moreover, incorporation of the construct within a viral vector, such as an adenovirus, appears to enhance expression.

Accordingly, it is expected that the MG 2 construct of the present invention will be useful in the therapy of AAT deficiencies, such as the liver and respiratory diseases associated therewith. Still further, the discovery of the importance of the role of Intron II in the AAT protein expression yield is useful for devising other vectors or minigenes for treating individuals having diseases relating to AAT deficiency. For example, as described herein, an AAT minigene is a cDNA construct having one or more introns.

The preferred construct of the present invention comprises an AAT cDNA having Intron II at its naturally occurring position in the gene. Advantageously, as with MG 2, a minigene so constructed is still small enough to fit in a retroviral or adenoviral vector. For this reason, the present invention solves the previous problems associated with cloning an AAT gene into a viral vector while maintaining an adequate level of expression for therapeutic treatment.

As mentioned above, diseases such as emphysema could be treated by, for example, preparing an inhalant comprising an adenovirus or retrovirus, engineered in accordance with the present invention, to produce AAT in high levels by the inclusion of Intron II. Once inhaled, the adenovirus will infect the cells of the alveoli and begin expressing AAT to protect against continued debilitation of the respiratory system due to the emphysema.

A similar therapeutic regime can be followed in the treatment of certain cases of cystic fibrosis. While AAT is present in patients having cystic fibrosis, it has been shown that its levels are reduced. Apparently, the extremely high levels of neutrophil elastase within such patients operate to overwhelm the AAT. Thus, the AAT is not present in sufficient quantities to protect the respiratory system of the patient from the enzymatic degradation.

Accordingly, by treating a patient with an expressible vector for AAT, debilatory effects of cystic fibrosis can be reduced.

Similarly, liver diseases associated with AAT deficiencies can be treated through either direct injection of the vector containing the minigene into the liver, or through ex vivo treatment of cells, followed by reinfusion of the cells to the liver. Through either method, it is expected that liver transplants, necessitated by the liver degeneration from AAT deficiencies, can be avoided.

Figure 3:
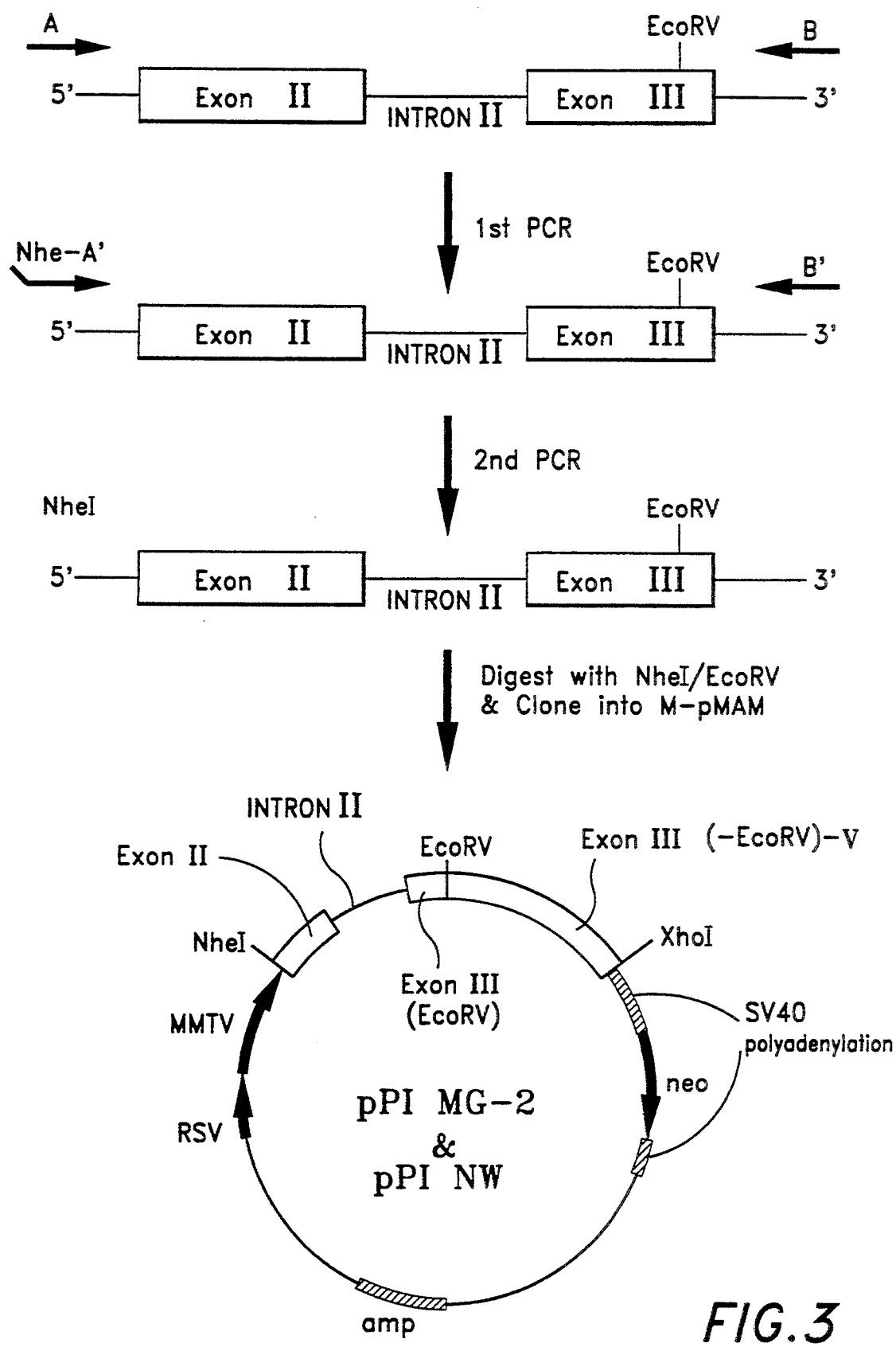
FIG. 3 is a diagram illustrating the cloning method of PCR amplification of the genomic DNA fragment having AAT Intron II. Amp, ampicillin resistance gene; MMTV-LTR, mouse mammary tumor virus long terminal repeat promoter; RSV, Rous sarcoma virus enhancer; neo, neomycin resistance gene.
Figure 4:
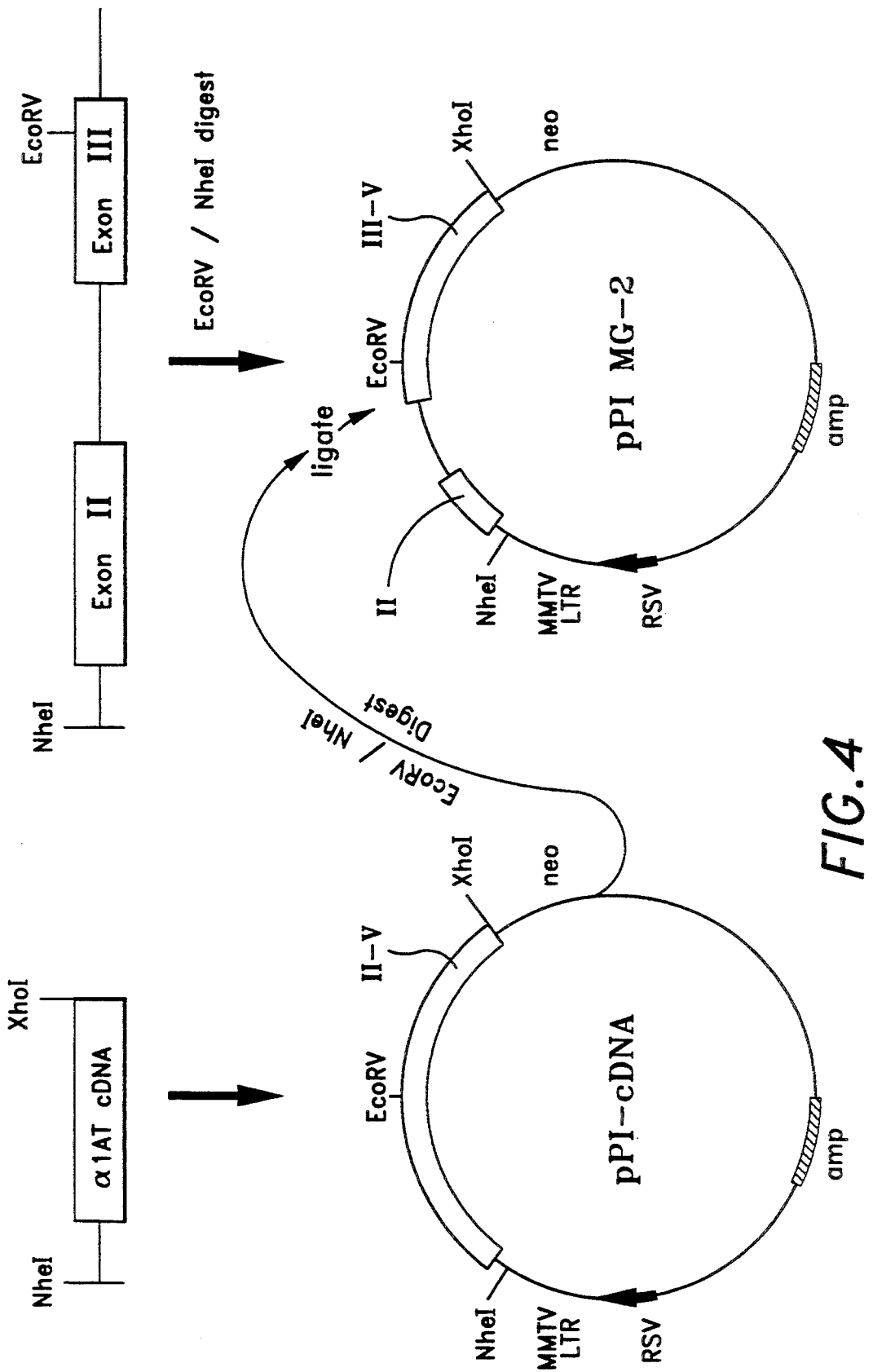
FIG. 4 is a diagram showing schematically the strategy used to prepare the AAT gene construct containing Exons II–V, with Intron II in its natural position with respect to Exons II and III and no other Introns (pPI-MG2) through digestion of an AAT cDNA at NheI/EcoRV restriction sites, and digestion of a PCR amplified fragment containing Exons II and III surrounding Intron I at the EcoRv/NheI restriction sites and ligation of the products.
Figure 5:
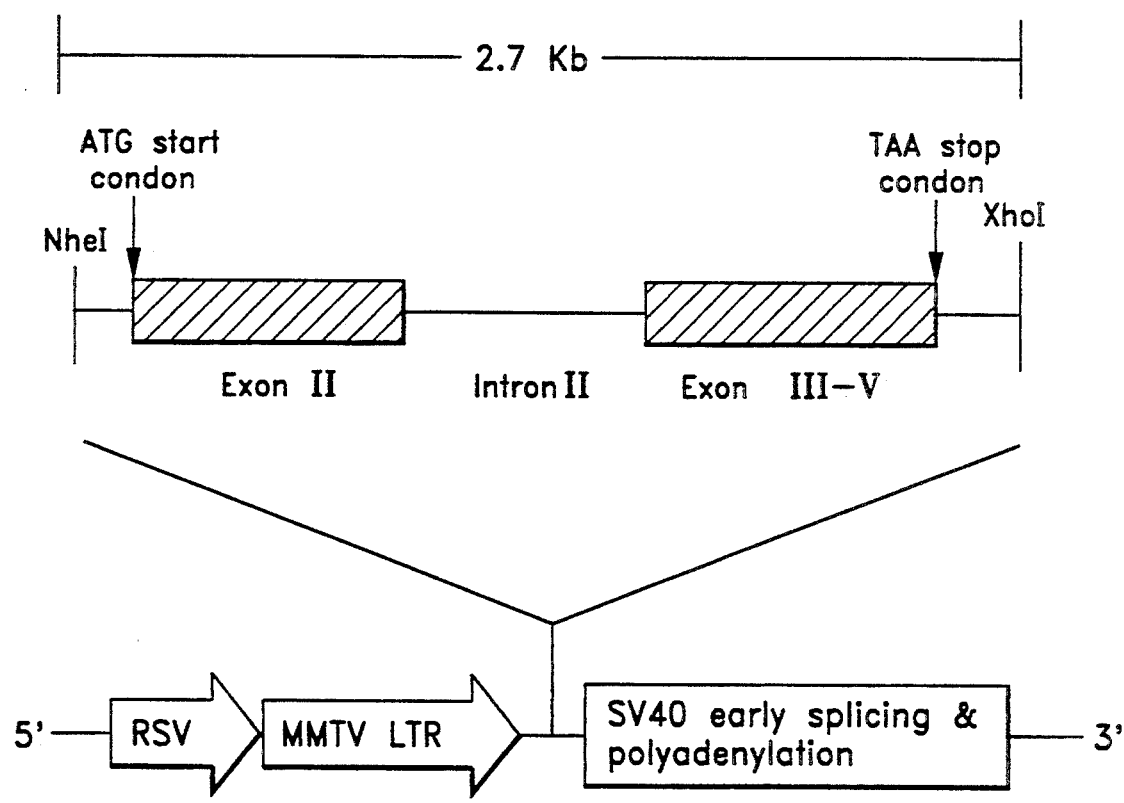
FIG. 5 is a detailed depiction of the MG2 expression cassette.
Figure 6:
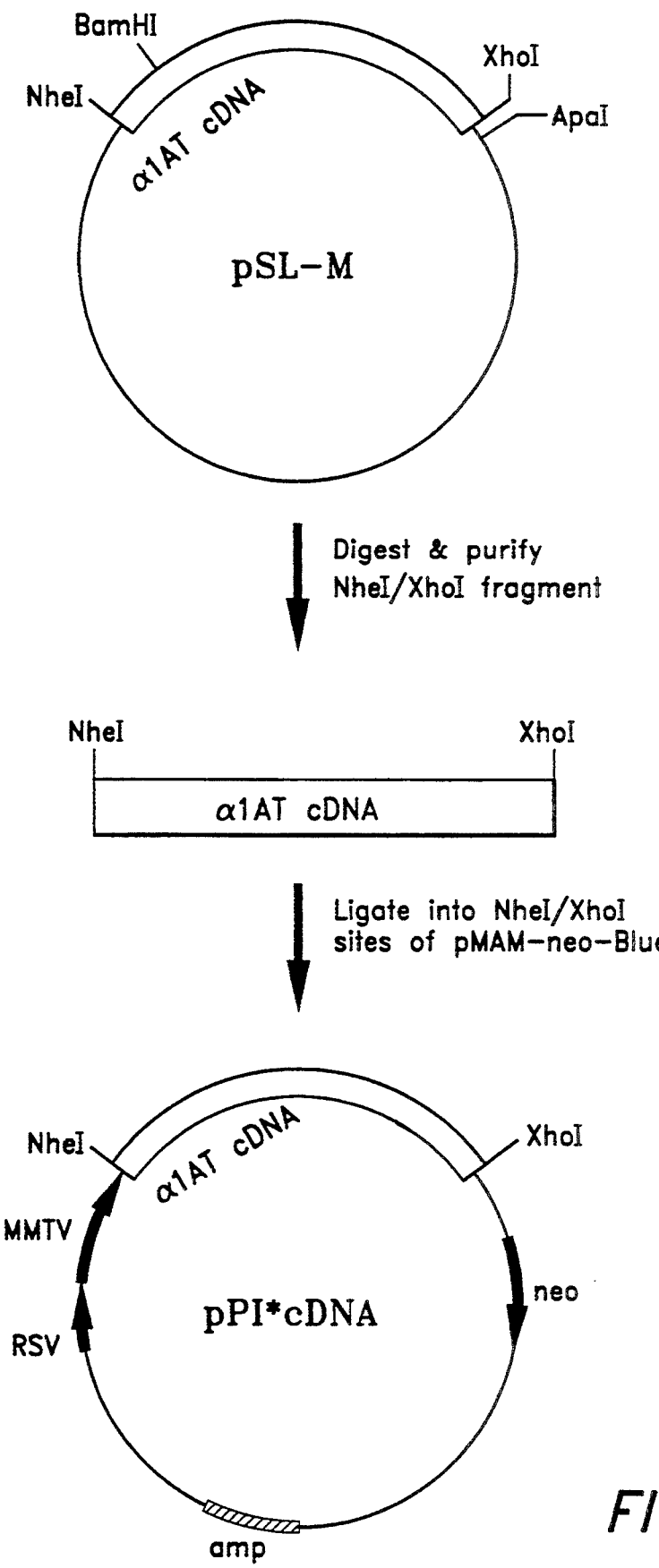
FIG. 6 is a schematic of the procedure used to make the pPI-cDNA construct.

To characterize the expression of AAT, we constructed a series of mammalian expression vectors. Essentially, expression vectors were constructed as shown in FIGS. 2-6. In FIG. 2, a schematic of the MG 2 construct is provided. In the MG 2 expression vector, Exon II was separated from Exons III through V by Intron II. In FIGS. 3 through 5, our strategy for the construction of the MG 2 expression vector is shown. Briefly, we derived the Exon II sequence and the initial Exon III sequence through the EcoRv restriction site of Exon III. The AAT gene was PCR amplified, followed by a second PCR amplification to include a NheI restriction site at the 5' end, 48 bp upstream from the start codon in Exon II. The product of the amplification was EcoRV and NheI digested and the Exon II/Intron II/Exon III (through EcoRV site) sequence was cloned into EcoRV ligated AAT cDNA, which was in turn cloned into M-pMAM plasmid. The M-pMAM plasmid contains two simian virus promoter sequences (SV40), a neomycin resistance gene (neo), an ampicillin resistance gene (amp), a rous sarcoma virus enhancer, and a mouse mammary tumor virus long terminal repeat promoter (MMTV LTR).

Similar strategies were followed for the preparation of constructs containing Intron III and Intron IV. These constructs were prepared in order to determine if enhanced expression of AAT could be obtained. Thus, in FIG. 6a and 6b, expression vectors for Exons II and III separated from Exons IV and V by Intron III and Exons II through IV separated from Exon V by Intron IV were prepared. Each of the vectors also contained ampicillin resistance gene (Amp), neomycin resistance gene (Neo), a Rous Sarcoma Virus promoter sequence, and an mouse mammary tumor virus long terminal repeat sequence (MMTV).

In the Experiments discussed below, and in the preparation of the above-discussed vectors, the following experimental protocols were employed.

mRNA Separation From Leukocytes: We used the Micro-Fast Track mRNA Isolation Kit (Invitrogen) as per the manufacturer's instructions. From whole blood, we isolated white blood cells using Plasmagel (Cellular Products, Inc.) in a 3:1 (whole blood:Plasmagel) ratio. A white blood cell fraction containing $10^6$ to $10^7$ cells was centrifuged and the pellet was washed once with 1×PBS. The pellet was resuspended in 1-2 ml of 1×TE and incubated with an equal volume of lysis buffer (1% SDS, 600 mM NaCl, 10 mM EDTA, 20 mM Tris, and 200 μg/ml proteinase K) at 42° C. for one hour.

The DNA was then sheared with a 21 gauge needle and the poly(A) mRNA was bound to oligo(dT) cellulose. After several washes in low salt buffer, to remove ribosomal RNA, the poly(A) mRNA was eluted by adding the solution to a spin-column tube and washing with elution buffer. RNA concentrations were measured by the DNA Dipstick Kit (Invitrogen) as instructed by the manufacturer.

Genomic DNA Separation From Leukocytes: Leukocytes were obtained as described above. Pellets were obtained as above and the cells were lysed, however, at 37° C. and overnight. The sample was then extracted once each with phenol, phenol/chloroform, and chloroform, followed by ethanol precipitation. The genomic DNA was spooled from the ethanol, air dried, and resuspended in 1×TE buffer. DNA purity was determined by UV spectroscopy at 260 nm and 280 nm.

Plasmid DNA Preparation: For large scale plasmid preparations used for cell transfection and sequencing Sambrook, J., Fritsch, E. F. & Maniatis, T. in "Molecular Cloning, A Laboratory Manual" (2d ed): pp. E.5. (Cold Spring Harbor Press, Cold Spring Harbor, N.Y., 1989), the disclosure of which is hereby incorporated by reference a single colony of E. coli or a frozen bacterial sample was inoculated into 10 ml Superbroth (Biofluids) containing 50 μg/ml ampicillin and shaken at 290 rpm at 37° C. for 6 hr. The inoculum was then transferred to 500 ml Superbroth-ampicillin and shaken overnight at 290 rpm. The cells were centrifuged and resuspended in 18 ml solution I (50 mM glucose, 25 mM Tris-cl pH 8.0, 10 mM EDTA). After cells were resuspended, 20 mg lysozyme (Sigma) was added followed by addition of 40 ml solution II (0.2N NaOH, 1% SDS) and 20 ml solution III (3M potassium acetate, 11.5% glacial acetic acid) and incubated on ice for 15 min.

After centrifugation, the supernatant was filtered through cheesecloth and the nucleic acids were precipitated by adding 0.6 volume of isopropanol. The solution was centrifuged and the pellet resuspended in 3 ml 1×TE. High molecular weight RNA was precipitated by addition of 3 ml 5 M LiCl and the nucleic acids were precipitated from the supernatant with isopropanol. The solution was centrifuged and the pellet resuspended in 500 μl 1×TE containing DNase-free RNase (20 μg/ml) and incubated at room temperature for 30 min. Upon precipitation of DNA by the addition of 1.6M NaCl containing 13% polyethylene glycol, and phenol/chloroform extraction, the DNA was ethanol precipitated, and dissolved in 500-1000 μl 1×TE. DNA concentrations were measured by UV spectrophotometry at wavelengths of 260 nm and 280 nm.

Plasmid Transformation: Competent E. coli were purchased from Gibco BRL and used in all transformations. Subcloning Efficiency DH5α competent cells were used for transformation of pMAMneo-Blue plasmids (Clontech), Bluescript II SK M13-plasmids (Stratagene), and pIBI20 plasmids (IBI) while MAX Efficiency DH5αFIQ competent cells were used for transformation of pSL1180 plasmids (Pharmacia).

1-3 μl from the ligation reaction was added to 100 μl of competent cells and incubated on ice for 30 min, heat-shocked for 45 sec at 42° C. and placed on ice for 2 min. 900 μl SOC medium (Digene) was added and cells were shaken at 225 rpm for 1 hr at 37° C. The cells were then spread onto LB agar plates (Digene) containing 50 μg/ml ampicillin and incubated overnight at 37° C. For transformations of pMAMneo-Blue plasmids, Bluo-gal (Gibco BRL) was present in the agar at 300 μg/ml. Transformed cells were stored by adding 1 ml log phase cell suspension in Superbroth to 70 μl DMSO and frozen on dry ice prior to transfer to liquid nitrogen.

Cloning of PCR DNA Fragments: PCR products were directly cloned using the TA Cloning System (Invitrogen). Briefly, the PCR product was ligated into the pCR II vector at a 1:3 (vector:insert) molar ratio using T4 DNA Ligase. 2 μl of the ligation reaction was added to 50 μl INVαF' competent cells and incubated on ice for 30 min followed by a heat-shock for 1 min at 42° C. and incubation on ice for 2 min. After adding 450 μl SOC medium, cells were shaken at 225 rpm at 37° C. for 1 hr, spread onto LB-agar plates containing 50 μg/ml ampicillin and 1 mg X-Gal (spread onto agar surface), and incubated overnight at 37° C. White colonies were then picked and grown for restriction enzyme analysis.

Ligations: Ligations were accomplished in a total reaction volume of 20 μl containing a total of 400 μg DNA in a 1:3 to 1:5 (vector:insert) ratio; ligation reactions were allowed to proceed at room temperature overnight using T4 DNA Ligase (Gibco BRL). Blunting was accomplished using Klenow fragment from DNA polymerase with no exonuclease activity. Usually, the ligated fragments were treated with calf intestinal alkaline phosphatase to prevent self-ligation.

Analysis of Plaques: Plaques were picked for analysis and depending on the quantity of analysis desired, were either grown up in 5 ml superbroth-ampicillin at 290 rpm at 37° C. for 6 hours or overnight, or minipreps were done using a Magic Miniprep Kit (Promega) per the manufacturer's instructions. Following preparation, an aliquot was digested using the appropriate restriction enzyme or enzymes and separated using 1% agarose gel electrophoresis.

Electrophoresis: The basic electrophoresis technique followed Sambrook, J., Fritsch, E. F. & Maniatis, T. in "Molecular Cloning, A Laboratory Manual" (2d ed): pp. E.5. (Cold Spring Harbor Press, Cold Spring Harbor, N.Y., 1989) the disclosure of which is hereby incorporated by reference and was conducted in a Gibco BRL model H5 at 65-100 volts. Agarose (IBI) was microwaved in 1×TAE buffer until dissolved, cooled to 60° C., and poured into the gel mold. Running buffer consisted of 1×TAE with 0.5 μg/ml ethidium bromide. DNA samples were electrophoresed in 1×loading buffer (0.5 mM Tris, pH 8.0, 50 μM EDTA, 5% glycerol, and 0.025% bromophenol blue). Molecular weight size markers used in all electrophoresis were from Gibco BRL (phi-X174 RF DNA/Hae III fragments, lambda DNA/Hind III fragments, or 100 bp DNA ladder).

To analyze small DNA fragments or to separate closely sized bands, polyacrylamide gel electrophoresis was performed (Sambrook et al supra 1989). To prepare 100 ml of a 5% acrylamide gel, 16.6 ml 30% acrylamide was combined with 72.7 ml water, 10 ml 10×TBE, 0.7 ml 10% ammonium persulfate, and 35 μl TEMED. Electrophoresis was done in a BioRad miniPROTEAN II apparatus at 50 volts in 1×TBE running buffer. DNA samples were electrophoresed with 1× loading buffer as described previously and stained with 0.5 μg/ml ethidium bromide after electrophoresis. Visualization of DNA was done on a UV light box and photographs were taken using Polaroid type 55 film.

Electrophoresis of immunoprecipitated $\alpha_1$-antitrypsin protein was performed on 7.5% SDS-polyacrylamide gels under denaturing conditions (Maniatis et al. supra 1989). To prepare the separating gel, 20 ml 1.5M Tris-Cl pH 8.8 was combined with 38.8 ml water, 20 ml acrylamide:bis (30:0.8), 0.8 ml 10% SDS, 0.4 ml 10% ammonium persulfate, and 40 μl TEMED. The separating gel was poured to within 1 cm of the comb bottom, overlaid with water, and allowed to polymerize for 2 hours. To prepare the stacking gel the following were combined: 5 ml 0.5M Tris-Cl pH 6.8, 2 ml acrylamide:bis (28:1.6), 0.2 ml 10% SDS, 12.8 ml water, 0.1 ml 10% ammonium persulfate, and 20 μl TEMED. The stacking gel was poured on top of the separating gel (after removing the overlaying water) and allowed to polymerize for 1.5 hours.

Just prior to loading, samples were heated at 95° C. for 5 min in 1×sample buffer (50 mM Tris-Cl pH 6.8, 2% SDS, 10% glycerol, 5% betamercaptoethanol, and 0.1% bromophenol blue). Protein molecular weight markers (Amersham) were also heated in sample buffer and loaded. Electrophoresis was done using a Gibco BRL model V16 vertical gel apparatus in Tris-glycine electrophoresis buffer (25 mM Tris, 250 mM glycine, and 0.1% SDS) at 90 volts until the dye passed into the separation gel and then 250 volts until the dye reached the bottom of the gel. After electrophoresis, the gel was fixed for 30 min in glacial acetic acid:isopropanol:water (10:25:65), soaked for 30 min in Amplify (Amersham), and dried under vacuum at 80° C. [$^{35}$S]-labeled proteins were visualized by flourography at $-70°$ C.

PCR Amplification: All PCR reactions were performed on a DNA thermal cycler using 10×buffer (500 mM KCl, 100 mM Tris-Cl pH 8.3, 15 μmM MgCl$_2$, 0.1% gelatin), dNTPs, and AmpliTaq (Perkin Elmer Cetus) as recommended by the manufacturer. For genomic DNA 100-50 ng DNA was used as template, and for plasmid DNA 5-10 ng DNA was used. A typical PCR reaction is as follows:

| DNA template | 5-500 ng |
| 5' Primer (20 μM) | 5 μl |
| 3' Primer (10 μM) | 5 μl |
| 10 X Buffer | 10 μl |
| dNTP (1.25 mM) | 16 μl |
| AmpliTaq (5U/μl) | 0.5 μl |
| Water | to 100 μl |

The reaction was overlaid with mineral oil prior to PCR.

The standard PCR conditions were as follows: an initial denaturation at 94° C. for 2 min followed by 25-40 cycles of (94° C./1 min denature, 50° C./2 min annealing, 72° C./3 min extension), and finished by a 7 min extension at 72° C. All samples were then stored at 4° C. until analyzed. For gel electrophoresis, samples were pipetted from under the oil and directly loaded onto the gel.

PCR Mutagenesis Method

To construct several α1-antitrypsin clones containing single base substitutions, PCR mutagenesis was used based on the method by Mullis et al. Nature 324:163–166 (1986) the disclosure of which is hereby incorporated by reference. Mutagenesis PCR primers were designed to be complementary to the α1AT sequence except for a single base difference in the center of the primer. The distal primers were designed to be complementary to an area of the α1AT cDNA plasmid clone such that the PCR products would be easily gel purified and restriction enzyme digested for cloning. In general, beginning with a normal α1-antitrypsin cDNA plasmid clone as template, two fragments overlapping at the mutagenesis primers were amplified by PCR. As will be discussed in greater detail in the following Experiments, one fragment was amplified from the 5' distal primer (A) to the mutagenesis primer (C), and the other fragment was amplified from the 3' distal primer (B) to the mutagenesis primer (C). The mutagenesis primers C and C' were exactly complementary to each other, and the resulting PCR products contained the single base substitution as defined by the sequence of the mutagenesis primers. The two PCR fragments were then gel purified and used in a 1:1 molar ratio as templates for a second PCR reaction, using only the distal primers (A and B). This second PCR reaction resulting in a single DNA product the length of which is defined by the distance between the distal primers. The second PCR product was then gel purified and cloned as described below.

Cloning of PCR mutagenesis fragments was accomplished in one of two ways. The PCR fragment may be restriction digested at two normally present restriction sites within the fragment (such as BamHI and XhoI in FIG. 10) and cloned into a plasmid at those restriction sites. Alternatively, one of the distal primers may be synthesized to contain a novel restriction site at its 5' end. This allows for sufficient binding of the primer to the template, and introduces the novel restriction site at the end of the PCR product.

Allele Specific Amplification

Allele specific amplification was performed essentially as described by Okayama et al. J. Lab. Clin. Med. 114:105–113 (1989) the disclosure of which is hereby incorporated by reference. Two allele specific PCR primers, one normal and one mutant, were constructed for each α1-antitrypsin null allele to be analyzed. Each primer pair differs only at the 3' termini, which corresponds to the mutational difference between the α1-antitrypsin normal allele and the null allele in question. Thus only a primer which is complementary at its 3' terminus will amplify. The distal primers were constructed to be complementary to an intronic sequence identical in both the normal and null alleles, and such that the PCR products can be easily identified by agarose gel electrophoresis.

For each α1-antitrypsin null allele being analyzed, two samples of genomic DNA (200 ng each) were amplified by PCR. One sample was amplified using the "normal" ASA primer in combination with the distal primer, and the other sample was amplified with the "mutant" ASA primer in combination with the distal primer. 10μl from each reaction as then electrophoresed on a 1% agarose gel in the presence of ethidium bromide and photographed using UV light at 300 nm.

Northern Blot Analysis of RNA

Norther blots (Alwine et al. Pro. Nat'l Acad. Sci USA 74:5350–5354 (1977); Methods Enzymol. 68:220–242 (1979) the disclosures of which are hereby incorporated by reference) were performed using a modified version described by Sambrook et al. supra (1989). Poly(A) mRNA isolated from NIH-3T3 cells or COS-1 cells (1 μg/lane) was combined with loading buffer (1.3×MOPS, 8.5% formaldehyde, 63% glycerol, 0.02% bromophenol blue), heated at 65° C. for 10 min, and electrophoresed on a 1% agarose gel under denaturing conditions (1.1% formaldehyde) at 90 volts until the dye ran ⅔ the length of the gel. The gel was then washed with water, stained with ethidium bromide, and washed again with water. A photograph was then taken under IV illumination on Polaroid type 55 film. After washing in 10×SSC, the gel was blotted overnight onto a positively charged nylon membrane (Boehringer Mannheim), and the RNA was bound to the membrane by UV-crosslinking using a UV Stratalinker (Stratagene). Prehybridization and hybridization to a [$^{32}$P]-labeled human α1AT CDNA was done as previously described.

Slot Blot Analysis of RNA

RNA slot blots (Kafatos et al. Nucl. Acids Res. 7:1541–1552 (1979); Thomas Proc. Nat'l Acad. Sci. 77:5201–5205 (1980)) the disclosures of which are hereby incorporated by reference were performed using a modified version described by Maniatis et al. supra (1989). Poly(A) mRNA was diluted in 15×SSC, heated at 65° C. for 10 min, and blotted onto a positively charged nylon membrane (Boehringer Mannheim) using a Schlecher & Schuell slot blot apparatus under low vacuum. Each slot was washed with 15×SSC and the membrane was then UV-crosslinked on a UV Stratalinker (Stratagene). Prehybridization and hybridization to a [$^{32}$P]-labeled human α1-antitrypsin cDNA was done as previously described.

Nuclear Run-On Transcription Analysis

Nuclei were isolated as described by Greenberg (1987). NIH-3T3 cells or COS-1 cells were washed with 1×PBS, scraped off of plates, and lysed by vortexing in lysis buffer (10 mM Tris-Cl pH 7.5, 10 mM naCl, 3 mM MgCl$_2$, 0.5% NP-40). After centrifuging 5 min at 500 g, the nuclei were resuspended in 200 μl glycerol storage buffer (50 mM Tris-Cl pH 8.0, 40% glycerol, 5 mM MgCl$_2$, 011 mM EDTA) and stored at −70° C. until used.

Nuclear run-ons were done as described by Pan et al. (1990). Transcripts were elongated with 100 μCi [$^{32}$P]-UTP (Amersham, 3000 Ci/mmol) in 40 mM Tris-Cl pH 8.0, 150 mM NH$_4$Cl, 7.5 mM MgCl$_2$, and 1 mM each of ATP, CTP, and GTP containing (1–5)×10$^7$ nuclei in a total volume of 400 μl and incubated at 30° C. for 35 min. RNA synthesis was terminated by incubating with 25 μl RNase-free DNase (Ambion, 2 U/μl) for 30 min at 30° C. followed by incubation with proteinase K (1 μg/μl), heparin (3 μg/μl), 10 mM Tris-Cl pH 7.5, 15 mM EDTA, and 3% SDS for 3 hr at 42° C. RNA was purified by phenol/chloroform extraction, trichloroacetic acid, and alcohol precipitation, further DNAse treatment, and then solubilized in 10 mM 1×TE. Samples were heated at 65° C. for 10 min prior to hybridization.

As a control, linear pMAMneo-Blue plasmid (Clontech) (10 μg/slot) or an equal amount of α1AT cDNA clone in pMAMneo-Blue were heated at 80° C. in 0.2N NaOH for 10 min, adjusted to 6×SSC, and applied to positively charged nylon membrane (Boehringer Mannheim) using a Schlecher & Schuell slot blot apparatus under low vacuum. Filters were baked for 2 hr at 80° C. under vacuum.

Metabolic Labeling and Immunoprecipitation

Cells were metabolically labeled according to Brantly et al (1988c). Cells (in 6 cm diameter culture plates) were washed 2× with 1×PBS (Biofluids) and starved for 15 min at 37° C. in 3 ml methionine-free DMEM (Biofluids). The medium was aspirated and the cells were pulsed for 30 min at 37° C. in 1 ml pulse media consisting of 300 $\mu$Ci [$^{35}$S]-methionine (Amersham, 1000 Ci/mmol), and 2 $\mu$M dexamethasone (Sigma) in methionine-free DMEM. Following the pulse, cells were washed 3× with 1×PBS and chased for 2 hr at 37° C. in 1 ml DMEM containing 10% FCS and 5-fold excess unlabeled methionine (USB). Cell lysates were harvested in 1 ml lysis buffer (1% NP-40, 0.5% sodium deoxycholate, 10 $\mu$g/ml aprotinin, and 1 mM PMSF in 1×PBS), frozen on dry ice, thawed on ice, and centrifuged at 4° C. to pellet cellular debris. Chase media (1 ml) was also collected and centrifuged. Samples were then immunoprecipitated immediately or stored in liquid nitrogen.

$\alpha_1$-antitrypsin was immunoprecipitated according to Maniatis et al supra (1989). 500 $\mu$l cell lysate or media was added to 300 $\mu$l NET-gel buffer (50 mM Tris-Cl pH 7.5, 150 mM NaCl, 0.1% NP-40, 1 mM EDTA, 0.25% gelatin, 0.02% sodium azide) and 10 $\mu$l rabbit anti-human $\alpha_1$-antitrypsin-antibody (Accurate Fine Chemicals and Scientific Co.) and rotated for >1 hr at 4° C. After antibody binding, 100 $\mu$l protein-A-sepharose CL-4B (Pharmacia) was added and rotated overnight at 4° C. The immunocomplexes were then washed with three wash solutions. The first wash consisted of NET-gel buffer supplemented with NaCl to a final concentration of 0.5M. The second wash consisted of NET-gel buffer supplemented with 0.1% SDS, and the third wash consisted of 10 mM Tris-Cl pH 7.5, 0.1% NP-40. Each wash consisted of adding 1.25 ml wash solution, 20 min rotation at 4° C. followed by centrifugation. After aspirating the final wash, 50 $\mu$l sample buffer (0.5M Tris-Cl, 10% SDS, 5% beta-mercaptoethanol, 10% glycerol, 0.5% bromophenol blue) was added, heated at 95° C. for 5 min, and electrophoresed as previously described.

Endoglycosidase H Digestion

Endoglycosidase H digestion of $\alpha_1$-antitrypsin was performed as described by Holt and Hart *J. Biol. Chem.* 261:8049–8057 (1986), the disclosure of which is hereby incorporated by reference, with modifications. Cells were metabolically labeled and the media was immunoprecipitated and washed as described above. To the immunocomplex was added 100 $\mu$l of 100 mM citrate pH 5.5, 0.1% SDS and incubated at 65° C. for 6 min. The sample was centrifuged and the supernatant transferred to a new tube containing 2 $\mu$l Pic 1 antiprotease cocktail (1 mg/ml leupeptin, 2 mg/ml antipain, and 10 mg/ml benzamidine dissolved in 10,000 units/ml of aprotinin) and 2 $\mu$l Pic 2 antiprotease cocktail (1 mg/ml chymostatin, 1 mg/ml papstatin, dissolved in dimethyl sulfoxide). The samples were mixed and divided into two tubes. To one tube was added 2 $\mu$l endoglycosidase H (Oxford Glycosystems, 40 mU) and to the other tube was added 2 ul water. All tubes were then incubated overnight at 30° C. 50 $\mu$l gel loading buffer was then added to each tube followed by heating at 95° C. for 5 min. The protein products were analyzed by 7.5% SDS-PAGE and flourography as described above.

Cell Culture and Transfection

NIH-3T3 cells (ATCC #CRL 1658) were maintained in DMEM supplemented with 10% FCS, 1×penicillin-streptomycin, and 2 mM glutamine (all purchased from Biofluids) at 37° C. and 10% $CO_2$. 15 hr prior to transfection, cells were trypsinized and plated at $1.2 \times 10^6$ cells per 6 cm plate for metabolic labeling or $1.5 \times 10^6$ cells per 10 cm plate for RNA isolation. Transfections were done as described by Maniatis et al supra (1989). 10 $\mu$g plasmid (for 6 cm plate) or 10 $\mu$g plasmid (for 10 cm plate) was transfected into log phase cells using the calcium-phosphate mediated transfection method (Graham and van der Eb, 1973) in the presence of chloroquine (Sigma) at a final concentration of 100 mM. Following 4 hr incubation at 37° C., cells were then washed with 1×PBS and incubated for 2 min at 37° C. in the presence of 3 ml 15% glycerol in 1×HBS (140 mM NaCl, 10 mM KCl, 1.5 mM $Na_2HPO_4$, 12 mM dextrose, and 30 mM HEPES). Cells were washed again with 1×PBS and incubated at 37° C. with DMEM media. Dexamethasone was added to each plate 48 hr after transfection at a final concentration of 2 $\mu$M to induce transcription from the MMTV-LTR promoter. After incubation for 24 hr in the presence of dexamethasone (72 hr post-transfection), cells were then harvested for RNA or metabolically labeled for protein analysis.

EXPERIMENT I. AAT cDNA PRODUCTION WITHOUT INTRONS

AAT cDNA without Introns was prepared in accordance with the procedures disclosed by Cortny et al. PNAS 81:669–673 (1984), the disclosure of which is hereby incorporated by reference. Briefly, mRNA was isolated from human blood leukocytes and reverse transcribed using oligo-dT primers. Following second strand synthesis, by standard well known methods, cDNA fragments were ligated into pMAMneo-Blue (Clontech).

EXPERIMENT II. PRODUCTION OF AAT PLASMID WITH INTRON II

We constructed an expression vector which had 48 bp of the 3' end of intervening sequence 1 (IVS1) (Intron I) from the endogenous AAT gene and included the cDNA sequence of Exons II-V and Intron II in its natural position, without Introns III and IV. As a first step we PCR amplified genomic DNA from human blood leukocytes.

PCR primers were derived from the AAT genomic DNA sequence as reported by Long et al. Biochemistry 23:4828–4837 (1984) the disclosure of which is hereby incorporated by reference. The following primers were used to PCR amplify the coding regions from genomic DNA that surround Intron II.

Primer A: 5'-T GCC TT GACT CGGGGCCT GG (SEQ ID NO: 1)
Primer B: 5'-CCT TCT GT CT TCAT TTT CCAGGAAC (SEQ ID NO: 2)

PCR Primer A (SEQ ID NO:1) binds with a sequence 48 bases upstream from the ATG start codon of $\alpha_1$-antitrypsin. Primer B (SEQ ID NO:2) binds with a sequence downstream from an endogenous EcoRV restriction site in Exon III (FIG. 4). PCR amplification was carried out by a thermal cycler and Taq polymerase (Perkin-Elmer).

The number of PCR amplification cycles varied from 15–30 cycles, with each cycle consisting of 1 minute at 94° C., 2 minutes at 60° C., and 3 minutes at 72° C. This method amplified the alpha$_1$-antitrypsin gene from 48 bp 5' of Exon II through Exon III, including the EcoRV restriction site.

After this first round of PCR we performed a second round of amplification with a 5' primer (Nhe-A') which was modified to contain the NheI restriction enzyme recognition site, and a 3' nested primer (B') as follows:

Primer Nhe-A': 5'-GCT AGC GCT AGC T GCC TT G ACT CGGGG CCT GG (SEQ ID NO: 3)
Primer B'    : 5'-CCT T CT GT CT T CAT TTT CCA GGA AC         (SEQ ID NO: 2)

This amplified molecule had a PCR-added 5' NheI site and an endogenous 3' EcoRV site. The resulting PCR product was cut with NheI/EcoRV to obtain a product having a NheI restriction site at its 5' end, 25 bp of Intron I, Exon II, Intron II, Exon III to the EcoRV restriction site.

A plasmid, pPI-cDNA (FIG. 6), was prepared contained 25 bp of the AAT sequence upstream of the ATG start codon in Exon II, a NheI restriction site at its 5' end, and Exons II–V, without introns in pMAMneo-Blue (Clontech). Plasmid pPI-cDNA was digested with NheI/EcoRV to remove the cDNA insert spanning the normal Intron II site.

Following 2% agarose gel purification, the cleaved pPI-cDNA was ligated to the PCR-amplified, NheI/EcoRV-digested, gene described above. This ligation produced pPI-MG2 having Intron II placed in its naturally occurring position followed by the remainder of the AAT coding sequence (without introns). See FIG. 4. The plasmid pPI-MG2 was deposited on Dec. 6, 1994 in accordance with the Budapest Treaty with the American Type Culture Collection, Rockville, Md., under Accession Number ATCC 69718.

EXPERIMENT III. PRODUCTION OF AAT PLASMID WITH INTRON III

Figure 7:
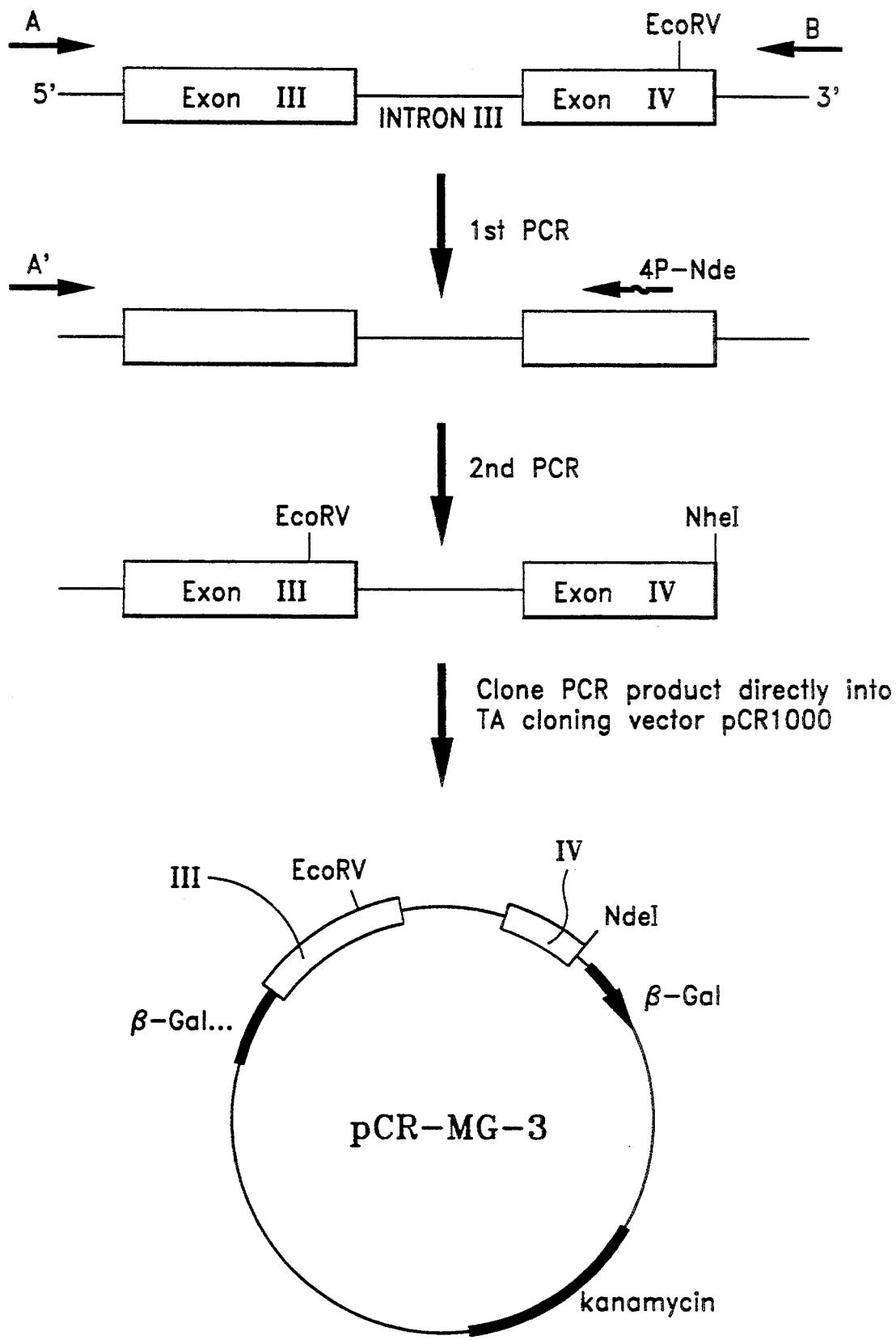
FIG. 7 is a schematic of the procedure used to prepare the plasmid pCR-MG-3, a precursor construct to the AAT construct containing Intron III.
Figure 10:
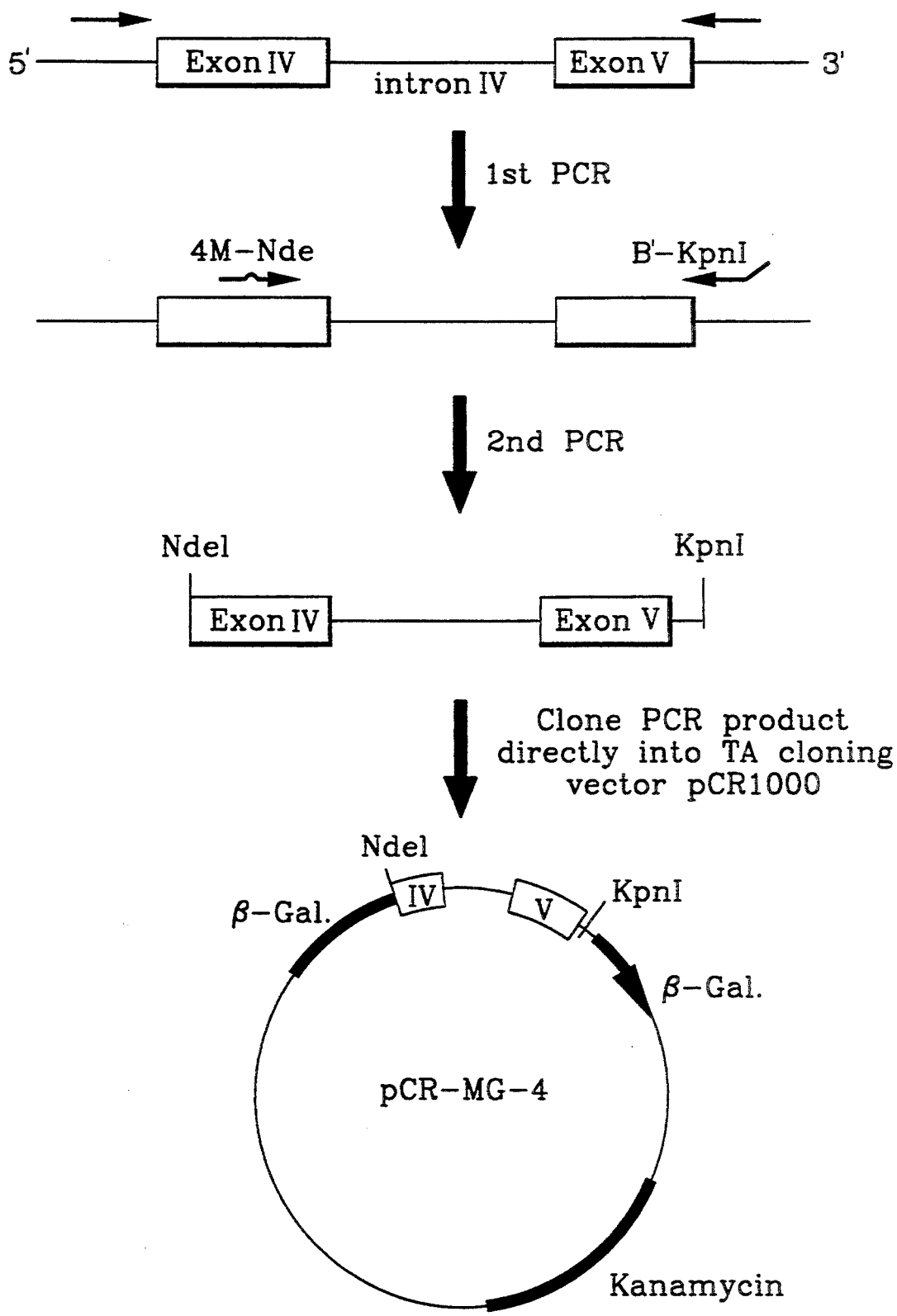
FIG. 10 is a schematic of the procedure used to prepare the plasmid pCR-MG-4 used in combination with the construct of FIG. 8 as a precursor construct to the AAT construct containing Intron IV.

As a control to Experiment II, we prepared 2 additional control vectors and tested their production of AAT relative to the plasmid pPI-MG2. Referring to FIGS. 7 and 10, plasmids pCR-MG-3 (containing Intron III) and pCR-MG-4 (containing Intron IV) (Experiment IV) were prepared as follows.

Plasmid pCR-MG-3

Referring to FIG. 7, to construct expression vectors of minigenes containing Intron III of the $\alpha_1$-Antitrypsin minigene construct was accomplished using the polymerase chain reaction to amplify genomic DNA spanning 45 bp 5' to the ATG of the $\alpha_1$-Antitrypsin gene and extending beyond the EcoRV restriction site in exon III. A first PCR was conducted from genomic DNA, as described above, using primers:

Primer A: 5'-CAT GGT TTC TT ATT CT GCT ACA CT  (SEQ ID NO: 4)
Primer B: 5'-TT CTT CCCT ACA GAT ACC ATG G      (SEQ ID NO: 5)

Then, a second PCR was used to insert a novel restriction site into exon IV of the cDNA because no convenient site is naturally present in Exon IV. Starting with an $\alpha_1$-antitrypsin normal cDNA as template, PCR mutagenesis was performed using mutagenesis primers 4P-Nde, and a 5' distal primer, as follows:

Primer 4P-Nde:  GCT CTT CAG ATC ATA TGT TCC AGT AAT GGAC (SEQ ID NO: 6)
Distal Primer:  GCT GAG TT CGC CTT CAC CT AT ACC GC       (SEQ ID NO: 7)

The mutagenesis primers were designed to alter the third, wobble base of codon 296 from C to A thus changing the sequence in that region to the recognition site for the restriction enzyme NdeI without altering amino acid 296. The PCR product was then directly ligated into the TA cloning vector pCR1000 to produce the clone pCR-MG-3 containing Intron III.

Plasmid pPI-cDNA.Nde

Figure 8:
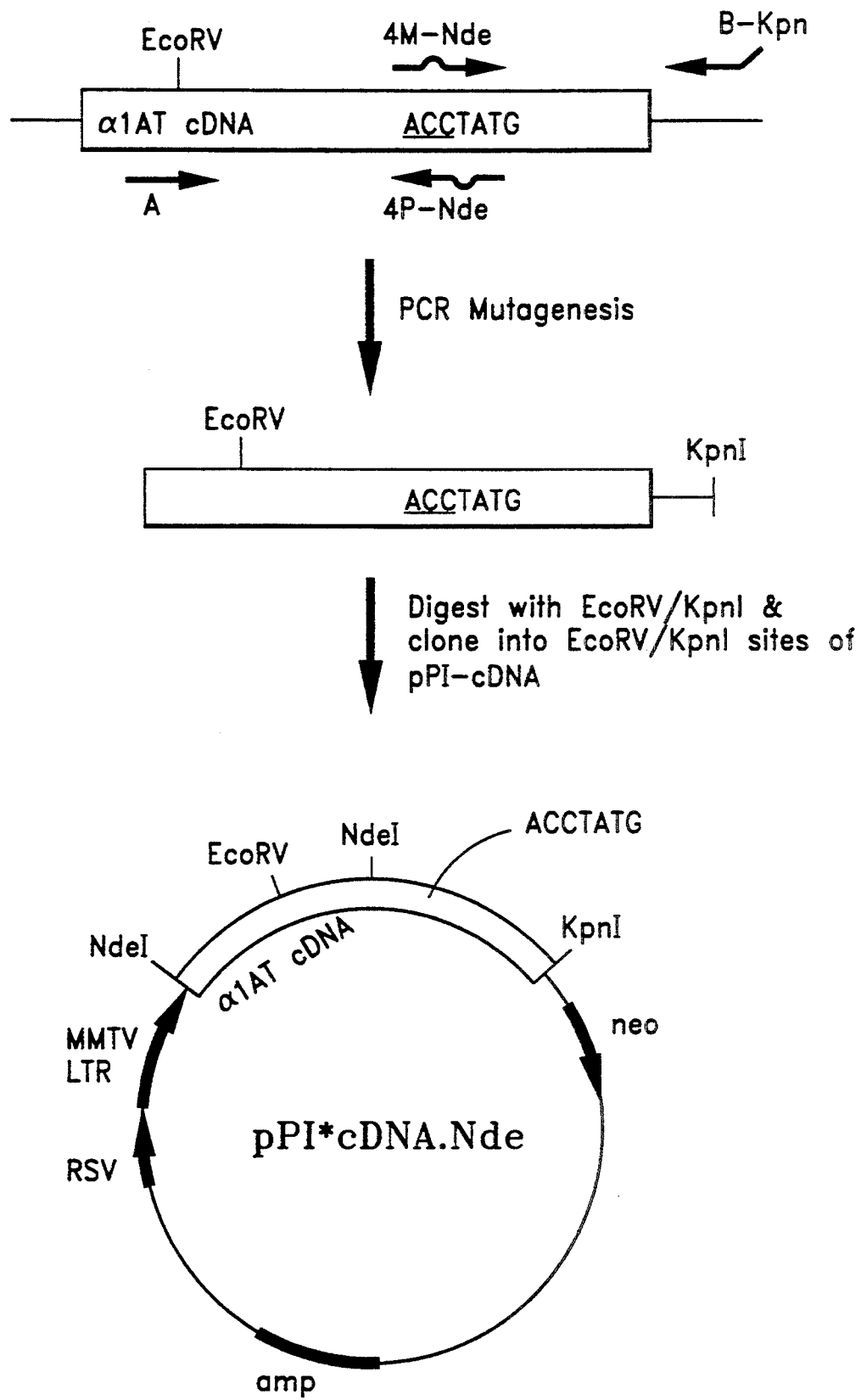
FIG. 8 is a schematic of the procedure used to prepare the plasmid pPI-cDNA.Nde used in combination with the construct of FIG. 7 as a precursor construct to the AAT construct containing Intron III.

Referring now to FIG. 8, another plasmid was prepared to allow the production of the AAT construct containing Exons II–V and only Intron III. Normal $\alpha_1$-antitrypsin cDNA was used as a template and PCR mutagenesis was performed using a 5' distal primer (A) upstream of the EcoRV site in Exon III, a 3' distal primer (B-Kpn) modified to contain the restriction site for KpnI, and two mutagenesis primers (4M-Nde and 4P-Nde), as follows:

Primer 4P-Nde:  GCT CTT CAG ATC ATA TGT TCC AGT AAT GGAC (SEQ ID NO: 6)
Distal Primer:  GCT GAG TT CGC CTT CAC CT AT ACC GC       (SEQ ID NO: 7)
Primer 4M-Nde:  GT CCA TT ACT GGA ACA TAT GAT CT GAA GAGC (SEQ ID NO: 8)
Distal Primer:  CCA TGG CCA TGG GAT TAC AGA TCA CAT GCA   (SEQ ID NO: 9)

The mutagenesis primers mutated the third base of codon 296 (ACC-ACA) which introduced a recognition site for the restriction enzyme NdeI without altering the amino acid encoded for. The PCR product was then cut with EcoRV/KpnI and cloned into the EcoRV/KpnI sites of pPI-cDNA to produce pPI-cDNA.Nde.

Cloning pCR-MG-3 and pPI-cDNA.Nde

Figure 9B:
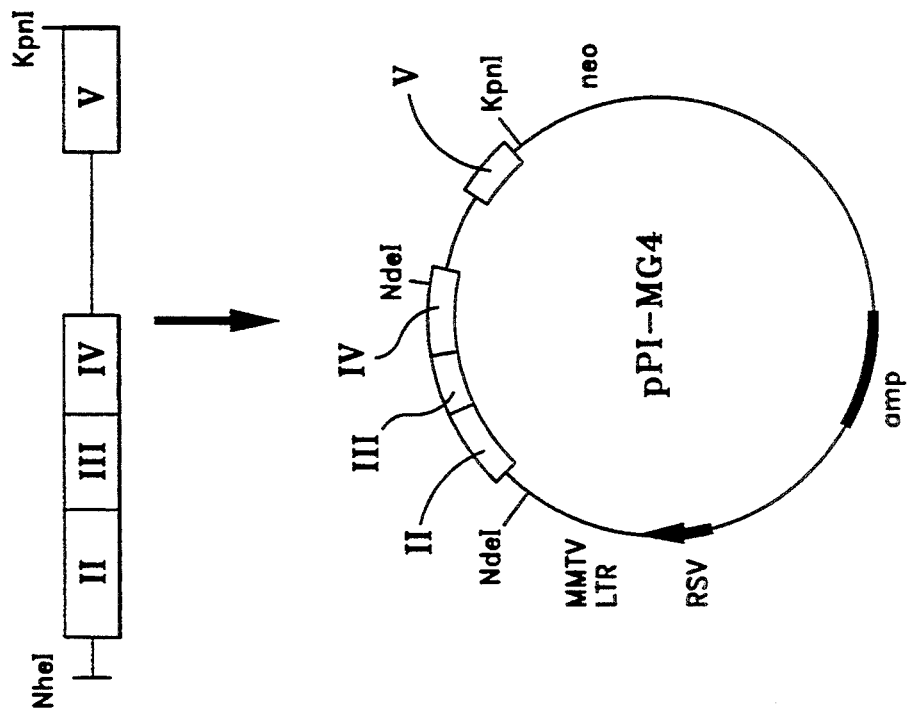
In FIG. 9b, a construct containing Exons II–V, with Intron IV in its natural position with respect to Exons IV and V and no other Introns (pPI-MG4).
Figure 9A:
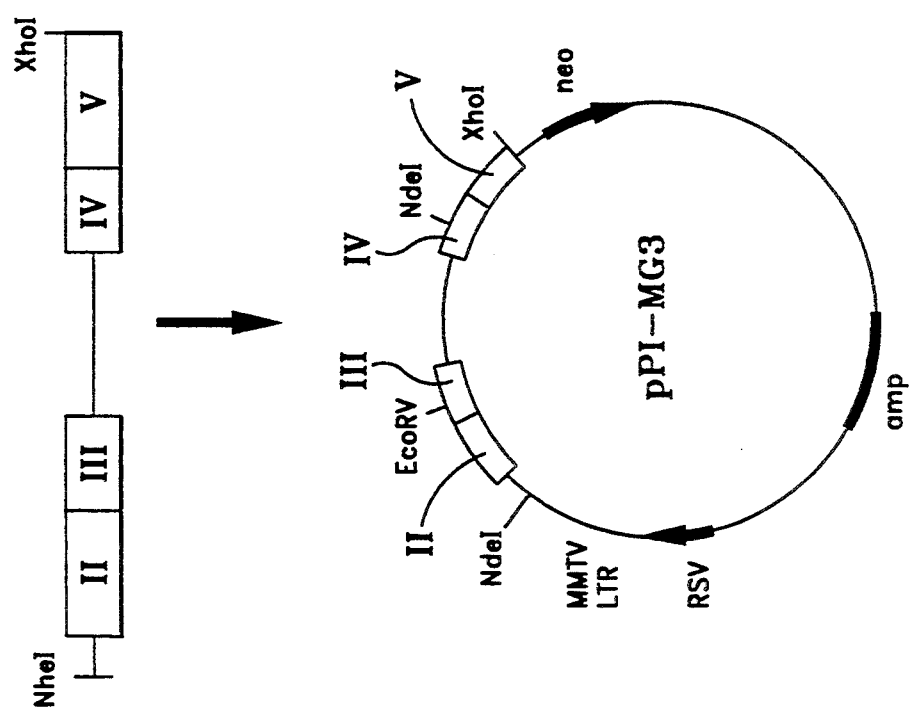
In FIG. 9a, a construct containing Exons II–V, with Intron III in its natural position with respect to Exons III and IV and no other Introns (pPI-MG3).

Plasmid pCR-MG-3 was EcoRV/NdeI digested and the EcoRV/NdeI fragment containing Intron III was agarose gel purified. Concurrently, the plasmid pPI-cDNA.Nde was subjected to NdeI/EcoRV digestion. Thereafter, the agarose purified EcoRV/NdeI fragment containing Intron III was cloned into pPI-cDNA.Nde to form the plasmid pPI-MG3. FIG. 9a.

EXPERIMENT IV. PRODUCTION OF AAT PLASMID WITH INTRON IV

The plasmid pCR-MG-4 (containing Intron IV) was prepared as follows:

Plasmid pCR-MG-4

Referring to FIG. 10, to construct expression vectors of minigenes containing intron III of the $\alpha_1$-Antitrypsin minigene construct was accomplished using the polymerase chain reaction to amplify genomic DNA spanning Exons IV–V. In a first PCR amplification, primers A and B that flank each Exon were used:

Primer A: 5'-CACTTGCACTGTGGTGGGTCCCAG (SEQ ID NO: 10)
Primer B: 5'-CAGAGAAAACATGGGAGGGATTTACA (SEQ ID NO: 11)

A second amplification was performed, similar to that in Experiment III, using a nested 3' primer (B'-KpnI) which was altered to contain the KpnI restriction site, and a 5' mutagenesis primer 4M-Nde. The 4M-Nde primer introduced the NdeI restriction site in Exon IV as described above:

Primer 4M-Nde: GTCCATTACTGGAACATATGATCTGAAGAGC (SEQ ID NO: 8)
Distal Primer: CCATGGCCATGGGATTACAGATCACATGCA (SEQ ID NO: 9)

The PCR product was directly ligated into the TA cloning vector pCR1000, producing the clone pCR-MG-3.

Cloning pCR-MG-4 and pPI-cDNA.Nde

Referring again to FIG. 8, as in Experiment III, the pPI-cDNA.Nde plasmid was again used for cloning.

Plasmid pCR-MG-4 was EcoRV/NdeI digested and the KpnI/NdeI fragment containing Intron IV was agarose gel purified. Concurrently, the plasmid pPI-cDNA.Nde was subjected to NdeI/KpnI digestion. Thereafter, the agarose purified KpnI/NdeI fragment containing Intron IV was cloned into pPI-cDNA.Nde to form the plasmid pPI-MG4. FIG. 9b.

EXPERIMENT V. QUANTIFICATION OF $\alpha_1$-ANTITRYPSIN GENE EXPRESSION FROM pPI-MG 2–4

$\alpha_1$-Antitrypsin gene expression from the vectors prepared in Experiments II through IV (MG 2–4) was determined by quantifying protein secretion and mRNA content in COS I and/or NIH 3T3 cells (ATCL No. CRL 1658) following transient expression of the transfected $\alpha_1$-Antitrypsin vectors. The secretion was quantified following metabolic labeling, immunoprecipitation, and SDS gel electrophoresis. $\alpha_1$-Antitrypsin mRNA content was evaluated using northern and slot blot analysis of transfected cellular RNA, $\alpha_1$-antitrypsin RNA and protein expression was $\geq 3$ fold and up to 10 fold more for MG 2 transfected cells as compared to cells transfected with the $\alpha_1$-antitrypsin cDNA.

Figure 11:
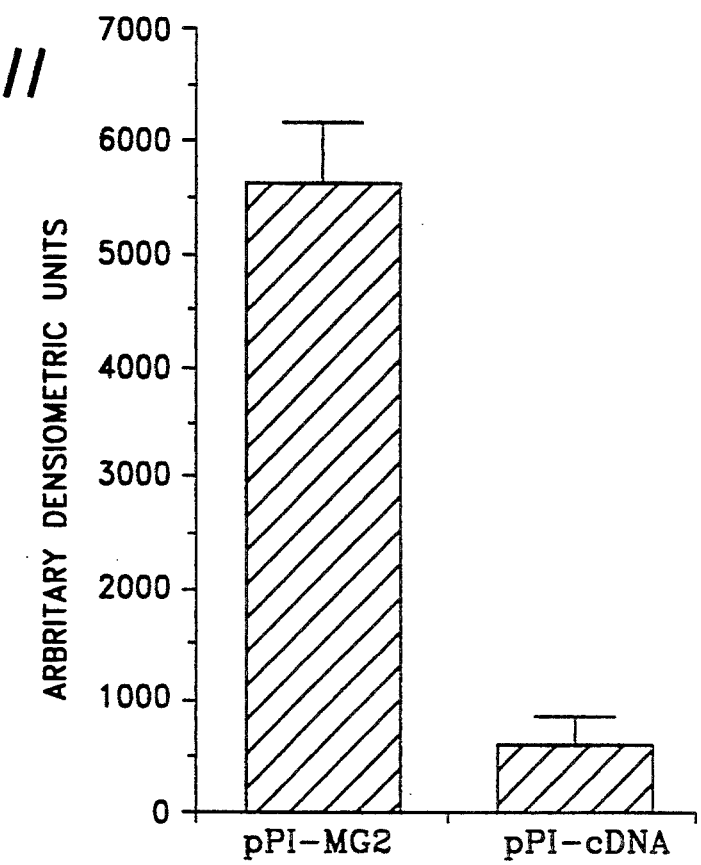
FIG. 11 is a bar graph showing the enhancement of expression of secreted AAT from the construct pPI-MG2 (as shown in FIG. 4) in comparison to pPI-cDNA (FIG. 6) in NIH 3T3 cells.
Figure 12:
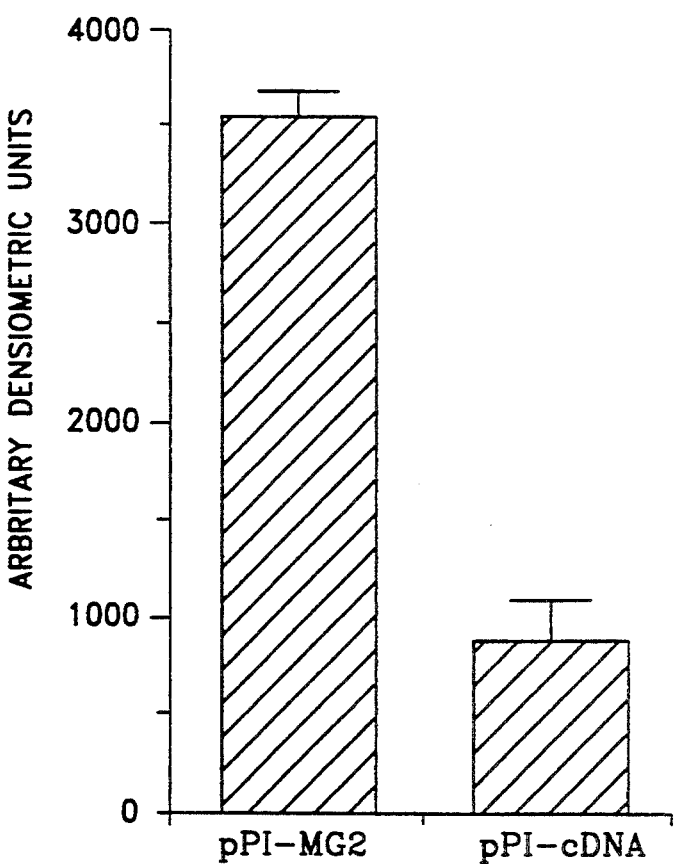
FIG. 12 is a bar graph showing the enhancement of expression of secreted AAT from the construct pPI-MG2 (as shown in FIG. 4) in comparison to pPI-cDNA (FIG. 6) in NIH 3T3 cells.

In FIG. 11, the enhancement in expression of AAT protein is dramatically shown, demonstrating the activity of the MG 2 construct as compared to pPI-cDNA. The results are taken from a Northern blot comparing the quantity of AAT protein formed by NIH 3T3 cells through the use of arbitrary densitometric units. Similarly, In FIG. 12, mRNA expression from NIH 3T3 cells show similar enhanced production when exposed to MG 2 as compared to exposure to pPI-cDNA.

Figure 13:
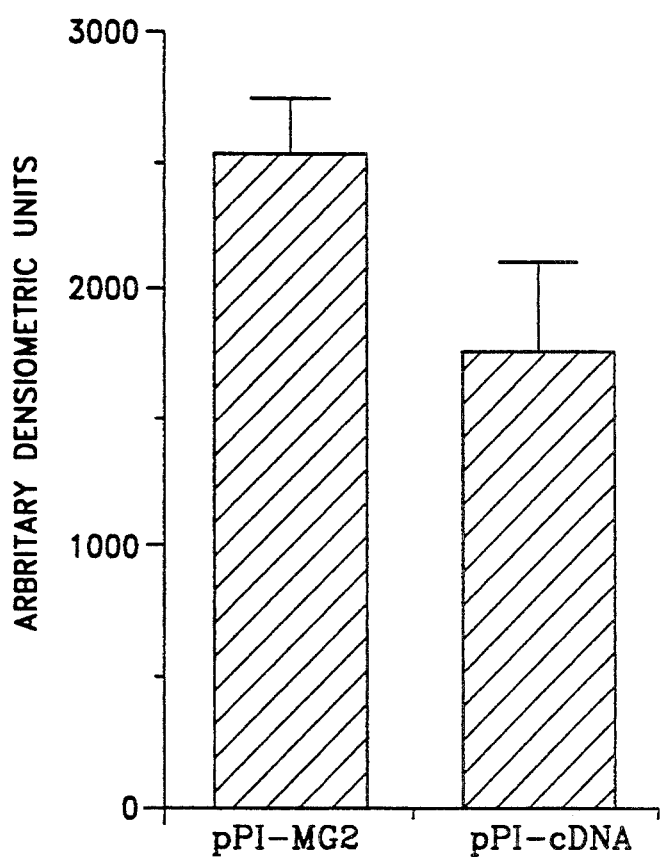
FIG. 13 is a bar graph showing the enhancement of gamma-actin mRNA from the construct pPI-MG2 (as shown in FIG. 4) in comparison to pPI-cDNA (FIG. 6) in NIH 3T3 cells.

Gamma-actin mRNA production is also enhanced in NIH 3T3 cells due to exposure to MG 2 as compared to cells exposed to pPI-cDNA. Gamma-actin acts as a control for the total RNA expressed. These results are shown in FIG. 13.

Figure 14:
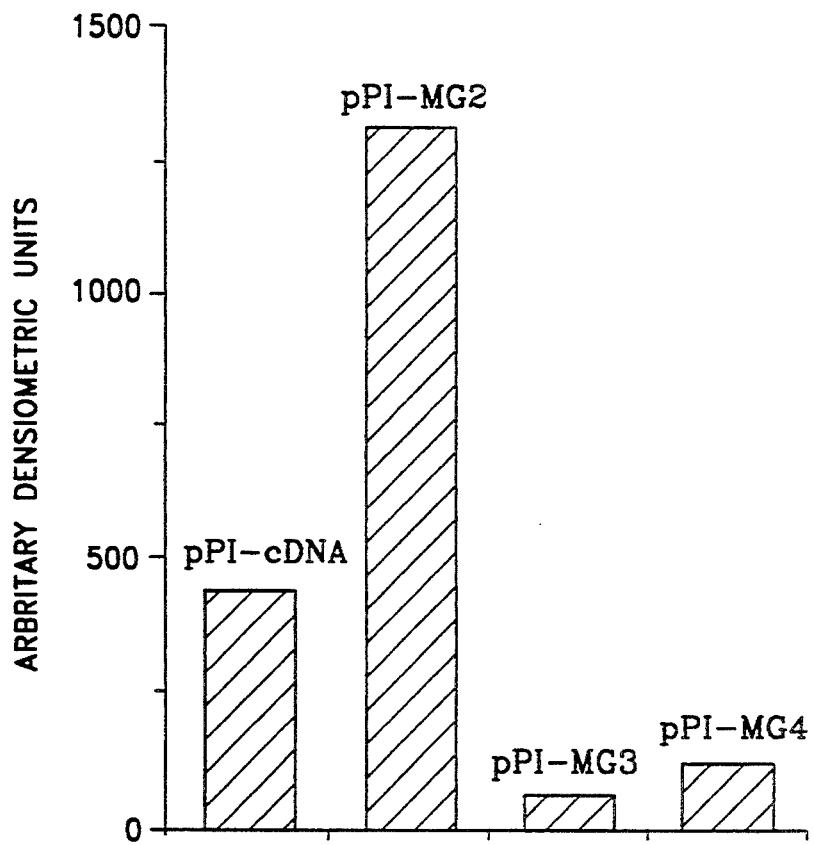
FIG. 14 is a bar graph showing the enhancement of expression of secreted AAT from the construct pPI-MG2 (as shown in FIG. 4) in comparison to pPI-cDNA (FIGURE 8), pPI-MG3 (FIG. 9a), and pPI-MG4 (FIG. 9b) in NIH 3T3 cells.

In FIG. 14, a comparison is provided that shows the dramatic contrast between MG 2 expression of AAT protein as compared to pPI-cDNA and MG's 3 and 4, again in NIH 3T3 cells.

The enhancement of gene expression from the MG 2 vector was observed regardless of cell type. This finding eliminates the possibility that a cell specific expression process occurs. Comparison of $\alpha_1$-Antitrypsin secretion from cells transfected with MG 3 and MG 4 demonstrated that the enhanced gene expression was specific for the vector containing IVS II (i.e., Intron II). Furthermore, comparison of $\alpha_1$-antitrypsin secretion among permanent COS I cell lines containing these vectors show similar results and demonstrate that the enhancement in gene expression is not transient in nature.

These observations are indicative that an element or elements within the second intervening sequence of the AAT gene (Intron II) acts to control $\alpha_1$-Antitrypsin gene expression rather than a more general mechanism associated with RNA transport or stability. $\alpha_1$-Antitrypsin retroviral shuttle vectors containing Intron II or the $\alpha_1$-Antitrypsin cDNA alone transfected into CHO cells demonstrate that the Intron II containing shuttle vector transfected cells secreted 6–10 fold more $\alpha_1$-Antitrypsin as compared to the cDNA without Intron II. This finding illustrates the probable utility of Intron II containing $\alpha_1$-antitrypsin constructs for genetic therapy of $\alpha 1AT$ deficiency.

EXPERIMENT VI. DETERMINATION OF EXPRESSION PROMOTING REGION IN INTRON II

As will be appreciated, in many situations, less than the entire sequence of a gene is required for expression and/or enhancement of expression, as the case may be. Accordingly, in order to determine the shortest sequence of Intron II required for the enhancement of expression, we will conduct allele specific amplification and PCR mutagenesis, as described above. In this manner, we will be able to determine which sequence or sequences in the Intron II sequence that are required for the enhancement of expression.

Additionally, when points of interest (either that depress or enhance expression) are found in the Intron II sequence, we will prepare PCR primers to introduce restriction sites into various regions in the Intron II sequence. These can then be digested and ligated into plasmids as discussed in Experiments II through IV and clones can be tested for activity as described above.

EXPERIMENT VII. PREPARATION OF A RETROVIRAL VECTOR OF MG2

Figure 15:
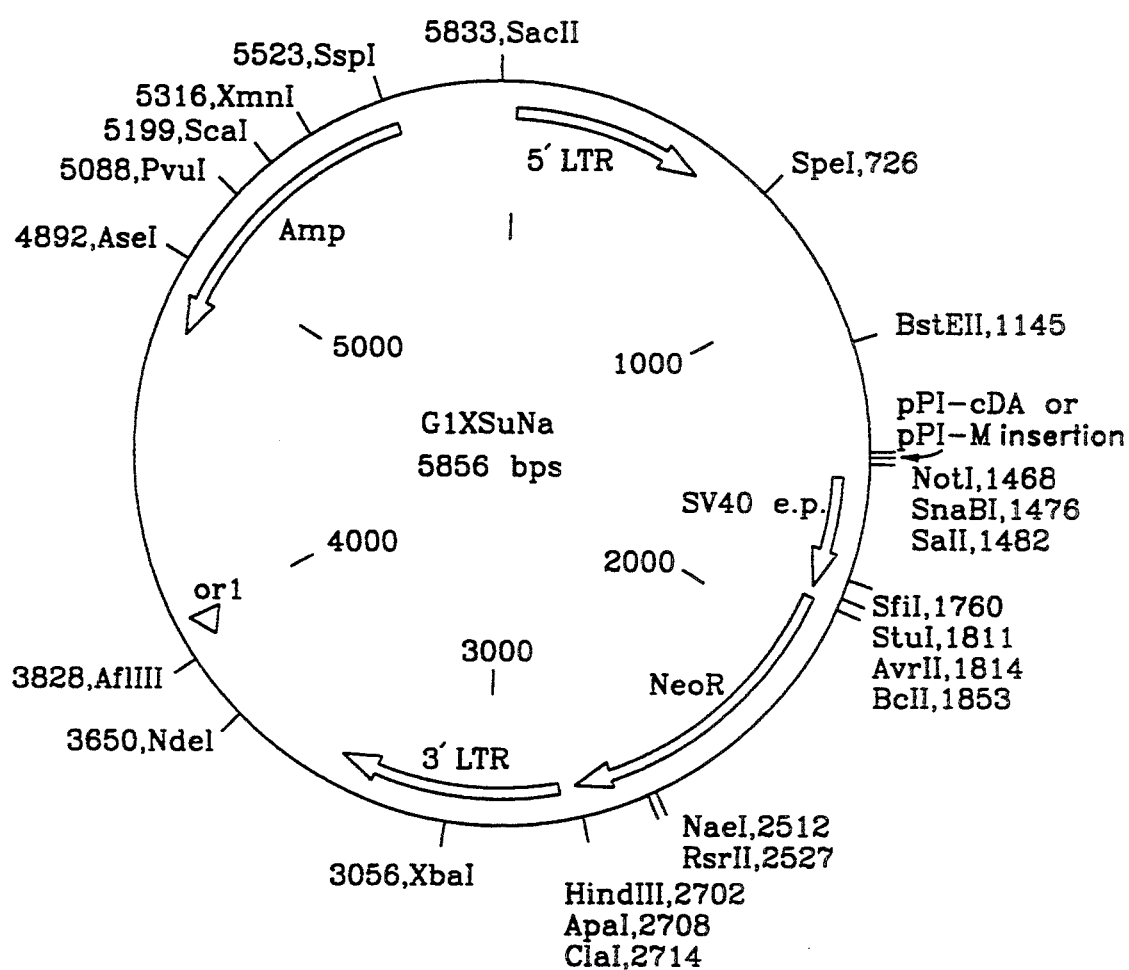
FIG. 15 is a schematic of the retrovirus G1XSvNa used to create viral vector products in accordance with one aspect of the present invention.

We prepared a retroviral expression vector containing the MG 2 construct in the following manner. Out of the plasmid pPI-MG2, we digested the MG2 sequence out through the use of NheI/HindIII or NheI/XhoII digestion. Concurrently, we prepared and cloned a cDNA/PIBI plasmid (I.B.I.), that we digested the AAT cDNA out. Also, we cleaved, at an insertion position, a retroviral vector, G1X-SvNa, with enzyme SalI at base 1482. FIG. 15.

Once all of the above starting constructs are readied, the G1×vector, the AAT cDNA insert, and MG2 insert are blunted with Klenow fragment of DNA Polymerase I (GIBCO, BRL) in an appropriate buffer, as described above. Also, the 5' phosphate groups are removed from the blunted G1×vector with calf intestinal alkaline phosphotase (CIP) (New England BioLabs). Thereafter, the MG2 construct and the cDNA inserts are ligated into the separate vectors using T4 DNA ligase (GIBCO/BRL), as above.

DH5-alpha competent cells were then transformed with the ligation mixture and the cells were plated on ampicillin containing medium and allowed to grow into colonies. Positive colonies were picked (based on their ampicillin resistance) and transferred to test tubes containing DMEM and 5% FBS.

Confirmation of positive clones was accomplished using restriction digests of miniprep DNA as described above, and through PCR. Also, we sequenced the vector/insert junctions to further confirm the positive insertion of the construct in the vector. Further discussion of the preparation of viral vectors can be found in Lemarchand et al. *Proc. Nat'l Acad. Sci. USA* 89(14):6482–6486 (1992) the disclosure of which is hereby incorporated by reference.

EXPERIMENT VIII. MEASUREMENT OF EXPRESSION OF AAT PROTEIN FROM VIRAL VECTOR CONTAINING MG 2

HeLa cells are transfected in a similar manner as in Experiment VI with the viral vector prepared in accordance with Experiment VII. The cells are grown in DMEM with 10% FBS after infection for four hours and assayed at 72 hours. Thereafter, AAT mRNA expression is measured by Slot blot and Northern blot. Enhanced expression of AAT mRNA cells that are transfected with the MG2 containing vector as compared to the AAT cDNA vector is seen.

EXPERIMENT IX. IN VIVO TREATMENT FOR AAT DEFICIENCY IN THE LUNGS

The MG II construct may be used to treat $\alpha_1$-antitrypsin deficiencies in the lungs of patients. The MG II construct is of a manageable size for incorporation in a viral vector, such as a retroviral or adenoviral vectors. Moreover, our results in Experiments VI–VIII indicate that MG 2 is readily incorporated into viral vectors. Furthermore, the results in Experiment VIII demonstrate that equal, if not better, expression is attained through viral transfection of cells than in direct transfection of cells with an MG 2 construct. Accordingly, because of MG 2's high expression of AAT, it is predictable that alveolar uptake and expression will occur.

Viral vector systems have been indicated as highly efficient in transferring genes to mammals containing deficient genes. See, for example, Crystal *Am. J. Ned.* 92(6A): 44S–52S (1992); Lemarchand et al. Proc. Nat'l Acad. Sci. USA 89(14):6482-6486 (1992) the disclosures of which are hereby incorporated by reference.

The viral vector can also be conveniently administered to a patient. For example, administration may be accomplished through, for example, inhalation, liquid lavage, or through ex vivo treatment of cells, followed by reinfusion of such cells to the patient.

Formulation of Therapeutic Viral Vector Compositions: In order to administer the viral vectors including an MG, it will be appreciated that suitable carriers, excipients, and other agents may be incorporated into the formulations to provide improved alveolar transfer, and, hence expression of the MG.

A multitude of appropriate formulations can be found in the formulary known to all pharmaceutical chemists: Remington's Pharmaceutical Sciences, 15th Edition (1975), Mack Publishing Company, Easton, Pa. 18042. (Chapter 87: Blaug, Seymour). These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

Any of the foregoing formulations may be appropriate in the treatment with the viral vectors, provided that the viral particles are inactivated in the formulation and the formulation is physiologically compatible.

Typically, it is desirable to deliver approximately 50 viral vectors per cell to be treated. With the adeno virus, formulations should generally contain on the order of $10^{10}$ viral vectors per ml. With retrovirus, slightly different titers may be applicable. See Woo et al. *Enzyme* 38:207–213 (1987) the disclosure of which is hereby incorporated by reference. Additional assistance in determining appropriate dosage levels can be found in Kay et al. *Hum. Gene Ther.* 3:641–647 (1992); Liu et al. *Somat. Cell Molec. Genet.* 18:89–96 (1992); and Ledley et al. *Hum. Gene Ther.* 2:331–358 (1991) the disclosures of which are hereby incorporated by reference.

Administration of the Therapeutic Viral Vector Formulations: Depending upon the particular formulation that is prepared for the administration of the viral vectors, administration of the vectors can be accomplished through a variety of methods.

In a preferred embodiment, where the formulation is of appropriate viscosity, the formulations are inhaled, i.e., a fine mist of the virus containing formulation is generated that the patient inhales.

In another preferred embodiment, the formulation may be prepared for a liquid lavage sort of therapy.

EXPERIMENT X. LIVER TREATMENT

Where children manifest an AAT deficiency, the manifestation is usually in the liver. Typically, this currently necessitates a liver transplant. As will be understood, liver transplants are still very expensive and the clinical results are particularly uncertain. In addition, in adults, while the primary manifestation of AAT deficiencies is seen in the respiratory dysfunction due to an AAT deficiency, often liver dysfunction also attends.

While liver therapy in accordance with the present invention could probably be accomplished in a similar manner to lung therapy, it is currently more feasible to conduct ex vivo therapy of a biopsy sample of liver tissue, followed by reintroduction or reinfusion of such treated cells back into the patient to initiate in vivo therapy. The cells withdrawn in the biopsy are transfected with either a retroviral or adenoviral vector containing a construct of the present invention. The transfected biopsy cells are then allowed to proliferate to encourage viral replication and expression of AAT.

Thereafter, upon reinfusion, significant quantities of AAT will be produced.

The use of the construction vectors of the present invention will enable the treatment of these AAT deficient patients without the resort to liver transplant.

EXPERIMENT XI. LIPOSOME BASED DELIVERY

Liposomes are known to provide highly effective delivery of active agents to diseased tissues. For example, pharmacological or other biologically active agents have been effectively incorporated into liposomes and delivered to cells. Thus, constructs in accordance with the present invention can also be suitably formed in liposomes and delivered to selected tissues. Liposomes prepared from cationic lipids, such as those available under the trademark LIPOFECTIN (Life Technologies, Inc., Bethesda, Md.) are preferred.

Preferably, the liposome delivery can be accomplished in the lungs, in a similar manner as shown in Experiment IX. However, liposome delivery vehicles can also be suitably used in direct tissue treatment, i.e., through injection to an afflicted tissue or organ.

Particularly appealing to liposome based treatments is the fact that liposomes are relatively stable and possess relatively long lives, prior to their passage from the system or their metabolism. Moreover, liposome do not raise major immune responses.

Thus, in one aspect of the present invention a vector containing a construct of the invention is incorporated into a liposome and used for the delivery of the construct to a specific tissue. In a preferred respect, the liposome containing the construct is delivered to the lungs through inhalation or lavage type treatment. The liposome will aid the construct in transfecting a cell and becoming expressed by the cell, ultimately generating AAT protein and protecting the lungs.

In another aspect, the liposomes containing the constructs may be directly injected into a patient, such as into the patient's liver, and therapy will thereafter commence.

EXPERIMENT XII. DNA CONJUGATE DELIVERY SYSTEMS

DNA conjugates are newcomers to the genetic therapy delivery art. DNA conjugates typically contain a mass of DNA containing one or more expressible vectors coupled with a polyionic compound. In addition, the conjugates may be coupled to a transferon molecule, a transferon-like molecule, or other promotion factor. Still further, the conjugates can also be coupled with a viral capsid.

Similar modes of treatment are contemplated for DNA conjugates as those discussed in connection with Experiment XI.

---

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

TGCCTTGACT CGGGGCCTGG     20

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:2:

CCTTCTGTCT TCATTTTCCA GGAAC     25

( 2 ) INFORMATION FOR SEQ ID NO:3:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

GCTAGCGCTA GCTGCCTTGA CTCGGGGCCT GG    32

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:4:

CATGGTTTCT TATTCTGCTA CACT    24

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

TTCTTCCCTA CAGATACCAT GG    22

( 2 ) INFORMATION FOR SEQ ID NO:6:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:6:

GCTCTTCAGA TCATATGTTC CAGTAATGGA C    31

( 2 ) INFORMATION FOR SEQ ID NO:7:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:7:

GCTGAGTTCG CCTTCACCTA TACCGC 26

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:8:

GTCCATTACT GGAACATATG ATCTGAAGAG C 31

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:9:

CCATGGCCAT GGGATTACAG ATCACATGCA 30

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:10:

CACTTGCACT GTGGTGGGTC CCAG 24

(2) INFORMATION FOR SEQ ID NO:11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO ( x i ) SEQUENCE DESCRIPTION: SEQ ID NO:11:

CAGAGAAAAC ATGGGAGGGA TTTACA 26

( 2 ) INFORMATION FOR SEQ ID NO:12:

( i ) SEQUENCE CHARACTERISTICS:
        ( A ) LENGTH: 10627 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:12:

| | | | | | |
|---|---|---|---|---|---|
| AGATCTTGCT | ACCAGTGGAA | CAGCCACTAA | GGATTCTGCA | GTGAGAGCAG | AGGGCCAGCT | 60 |
| AAGTGGTACT | CTCCCAGAGA | CTGTCTGACT | CACGCCACCC | CCTGGACCTT | GGACACAGGA | 120 |
| CGCTGTGGTT | TCTGAGCCAG | GTACAATGAC | TCCTTTCGGT | AAGTGCAGTG | GAAGCTGTAC | 180 |
| ACTGCCCAGG | CAAAGCGTCC | GGGCACCGTA | GGCGGGCGAC | TCAGATCCCA | GCCAGTGGAC | 240 |
| TTAGCCCCTG | TTTGCTCCTC | CGATAACTGG | GGTGACCTTG | GTTAATATTC | ACCAGCAGCC | 300 |
| TCCCCGTTG | CCCCTCTGGA | TCCACTGCTT | AAATACGGAC | GAGGACAGGG | CCCTGTCTCC | 360 |
| TCAGCTTCAG | GCACCACCAC | TGACCTGGGA | CAGTGAATCG | TAAGTATGCC | TTTCACTGCG | 420 |
| AGGGGTTCTG | GAGAGGCTTC | TGAACTCCCC | ATGGCCCAGG | CAGGCAGCAG | GTCTGGGGCA | 480 |
| GGAGGGGGGT | TGTGGAGTGG | GTATCCGCCT | GCTGAGGTGC | AGGGCAGATG | GAGAGGCTGC | 540 |
| AGCTGAGCTC | CTATTTTCAT | AATAACAGCA | GCCATGAGGG | TTGTGTCCTG | TTTCCCAGTC | 600 |
| CTGCCCGGTC | CCCCCTCGGT | ACCTCCTGGT | GGATACACTG | GTTCCTGTAA | GCAGAAGTGG | 660 |
| ATGAGGGTGT | CTAGGTCTGC | AGTCCTGGCA | CCCCAGGATG | GGGGACACCA | GCCAAGATAC | 720 |
| AGCAACAGCA | ACAAAGCGCA | GCCATTTCTT | TCTGTTTGCA | CAGCTCCTCT | GTCTGTCGGG | 780 |
| GGCTCCTGTC | TGTTGTCTCC | TATAAGCCTC | ACCACCTCTC | CTACTGCTTG | GGCATGCATC | 840 |
| TTTCTCCCCT | TCTATAGATG | AGGAGGTTAA | GGTCCAGAGA | GGGGTGGGGA | GGAACGCCGG | 900 |
| CTCACATTCT | CCATCCCCTC | CAGATATGAC | CAGGAACAGA | CCTGTGCCAG | GCCTCAGCCT | 960 |
| TACATCAAAA | TGGGCCTCCC | CATGCACCGT | GGACCTCTGG | GCCCTCCTGT | CCCAGTGGAG | 1020 |
| GACAGGAAGC | TGTGAGGGGC | ACTGTCACCC | AGGGCTCAAG | CTGGCATTCC | TGAATAATCG | 1080 |
| CTCTGCACCA | GGCCACGGCT | AAGCTCATGC | GTGATTAAGC | CTCATAACCC | TCCAAGGCAG | 1140 |
| TTACTAGTGT | GATTCCCATT | TTACAGATGA | GGAAGATGGG | GACAGAGAGG | TGAATAACTG | 1200 |
| GCCCCAAATC | ACACACCATC | CATAATTCGG | GCTCAGGCAC | CTGGCTCCAG | TCCCCAAACT | 1260 |
| CTTGAACCTG | GCCCTAGTGT | CACTGTTTCT | CTTGGGTCTC | AGGCGCTGGA | TGGGGAACAG | 1320 |
| GAAACCTGGG | CTGGACTTGA | GGCCTCTCTG | ATGCTCGGTG | ACTTCAGACA | GTTGCTCAAC | 1380 |
| CTCTCTGTTC | TCTTGGGCAA | AACATGATAA | CCTTTGACTT | CTGTCCCCTC | CCCTCACCCC | 1440 |
| ACCCGACCTT | GATCTCTGAA | GTGTTGGAAG | GATTTAATTT | TTCCTGCACT | GAGTTTTGGA | 1500 |
| GACAGGTCAA | AAAGATGACC | AAGGCCAAGG | TGGCCAGTTT | CCTATAGAAC | GCCTCTAAAA | 1560 |
| GACCTGCAGC | AATAGCAGCA | AGAACTGGTA | TTCTCGAGAA | CTTGCTGCGC | AGCAGTCACT | 1620 |
| TCTTGGCATT | TTATGTGTAT | TTAATTTCAC | AATAGCTCTA | TGACAAAGTC | CACCTTTCTC | 1680 |
| ATCTCCAGGA | AACTGAGGTT | CAGAGAGGTT | AAGTAACTTG | TCCAAGGTCA | CACAGCTAAT | 1740 |
| AGCAAGTTGA | CGTGGAGCAA | TCTGGCCTCA | GAGCCTTTAA | TTTTAGCCAC | AGACTGACGC | 1800 |

| | | | | | | |
|---|---|---|---|---|---|---|
| TCCCCTCTTC | ATTTAGCCAG | GCTGCCTCTG | AAGTTTTCTG | ATTCAAGACT | TCTGGCTTCA | 1860 |
| GCTTTGTACA | CAGAGATGAT | TCAATGTCAG | GTTTTGGAGT | GAAATCTGTT | TAATCCCAGA | 1920 |
| CAAAACATTT | AGGATTACAT | CTCAGTTTTG | TAAGCAAGTA | GCTCTGTGAT | TTTTAGTGAG | 1980 |
| TTATTTAATG | CTCTTTGGGG | CTCAATTTTT | CTATCTATAA | AATAGGGCTA | ATAATTTGCA | 2040 |
| CCTTATAGGG | TAAGCTTTGA | GGACAGATTA | GATGATACGG | TGCCTGTAAA | ACACCAGGTT | 2100 |
| TTAGTAAGTG | TGGCAATGAT | GGTGACGCTG | AGGCTGATGT | TTGCTTAGCA | TAGGGTTAGG | 2160 |
| CAGCTGGCAG | GCAGTAAACA | GTTGGATAAT | TTAATGGAAA | ATTTGCCAAA | CTCAGATGCT | 2220 |
| GTTCACTGCT | GAGCAGGAGC | CCCTTCCTGC | TGAAATGGTC | CTGGGGAGTG | CAGCAGGCTC | 2280 |
| TCCGGGAAGA | AATCTACCAT | CTCTCGGGCA | GGAGCTCAAC | CTGTGTGCAG | GTACAGGGAG | 2340 |
| GGCTTCCTCA | CCTGGTGCCC | ACTCATGCAT | TACGTCAGTT | ATTCCTCATC | CCTGTCCAAA | 2400 |
| GGATTCTTTT | CTCCATTGTA | CAGCTATGAA | GCTAGTGCTC | AAAGAAGTGA | AGTCATTTAC | 2460 |
| CCCAGGCCCC | CTGCCAGTAA | GTGACAGGGC | CTGGTCACAC | TTGGGTTTAT | TTATTGCCCA | 2520 |
| GTTCAACAGG | TTGTTTGACC | ATAGGCGAGA | TTCTCTTCCC | TGCACCCTGC | CGGGTTGCTC | 2580 |
| TTGGTCCCTT | ATTTTATGCT | CCCAGGTAGA | AATGGTGTGA | GATTAGGCAG | GGAGTGGCTC | 2640 |
| GCTTCCTGT | CCCTGGCCCC | GCAAAGAGTG | CTCCCACCTG | CCCCGATCCC | AGAAATGTCA | 2700 |
| CCATGAAGCC | TTCATTCTTT | TGGTTTAAAG | CTTGGCCTCA | GTGTCCGTAC | ACCATGGGGT | 2760 |
| ACTTGGCCAG | ATGGCGACTT | TCTCCTCTCC | AGTCGCCCTC | CCAGGCACTA | GCTTTTAGGA | 2820 |
| GTGCAGGGTG | CTGCCTCTGA | TAGAAGGGCC | AGGAGAGAGC | AGGTTTTGGA | GTCCTGATGT | 2880 |
| TATAAGGAAC | AGCTTGGGAG | GCATAATGAA | CCCAACATGA | TGCTTGAGAC | CAATGTCACA | 2940 |
| GCCCAATTCT | GACATTCATC | ATCTGAGATC | TGAGGACACA | GCTGTCTCAG | TTCATGATCT | 3000 |
| GAGTGCTGGG | AAAGCCAAGA | CTTGTTCCAG | CTTTGTCACT | GACTTGCTGT | ATAGCCTCAA | 3060 |
| CAAGGCCCTG | ACCCTCTCTG | GGCTTCAAAC | TCTTCACTGT | GAAAGGAGGA | ACCAGAGTA | 3120 |
| GGTGATGTGA | CACCAGGAAA | GATGGATGGG | TGTGGGGAA | TGTGCTCCTC | CCAGCTGTCA | 3180 |
| CCCCCTCGCC | ACCCTCCCTG | CACCAGCCTC | TCCACCTCCT | TTGAGCCCAG | AATTCCCCTG | 3240 |
| TCTAGGAGGG | CACCTGTCTC | ATGCCTAGCC | ATGGGAATTC | TCCATCTGTT | TTGCTACATT | 3300 |
| GAACCCAGAT | GCCATTCTAA | CCAAGAATCC | TGGCTGGGTG | CAGGGGCTCT | CGCCTGTAAC | 3360 |
| CCCAGCACTT | TGGGAGGCCA | AGGCAGGCGG | ATCAAGAGGT | CAGGAGTTCA | AGACCTGCCT | 3420 |
| GGCCAACACG | GTGAAACCTC | AGCTCTACTA | AAAATACAAA | AATTAGCCAG | GCGTGGTGGC | 3480 |
| ACACGCCTGT | AATCCCAGCT | ATTTGGGAAG | CTGAGACAGA | AGAATTTCTT | GAACCCGGGA | 3540 |
| GGTGGAGGTT | TCAGTGAGCC | GAGATCACGC | CACTGCACTC | CACCCTGGCG | GATAAAGCGA | 3600 |
| GACTCTGTCT | CAAAAAAAAC | CCAAAAACCT | ATGTTAGTGT | ACAGAGGGCC | CCAGTGAAGT | 3660 |
| CTTCTCCCAG | CCCCACTTTG | CACAACTGGG | GAGAGTGAGG | CCCCAGGACC | AGAGGATTCT | 3720 |
| TGCTAAAGGC | CAAGTGGATA | GTGATGGCCC | TGCCAGGCTA | GAAGCCACAA | CCTCTGGCCC | 3780 |
| TGAGGCCACT | CAGCATATTT | AGTGTCCCCA | CCCTGCAGAG | GCCCAACTCC | CTCCTGACCA | 3840 |
| CTGAGCCCTG | TAATGATGGG | GGAATTTCCA | TAAGCCATGA | AGGACTGCAC | AAAGTTCAGT | 3900 |
| TGGGAAGTGA | AAGAGAAATT | AAAGGGAGAT | GGAAATATAC | AGCACTAATT | TTAGCACCGT | 3960 |
| CTTTAGTTCT | AACAACACTA | GCTAGCTGAA | GAAAAATACA | AACATGTATT | ATGTAATGTG | 4020 |
| TGGTCTGTTC | CATTTGGATT | ACTTAGAGGC | ACGAGGGCCA | GGAGAAAGGT | GGTGGAGAGA | 4080 |
| AACCAGCTTT | GCACTTCATT | TGTTGCTTTA | TTGGAAGGAA | ACTTTTAAAA | GTCCAAGGGG | 4140 |
| GTTGAAGAAT | CTCAATATTT | GTTATTTCCA | GCTTTTTTTC | TCCAGTTTTT | CATTTCCCAA | 4200 |
| ATTCAAGGAC | ACCTTTTTCT | TTGTATTTTG | TTAAGATGAT | GGTTTTGGTT | TTGTGACTAG | 4260 |

| | | | | | | |
|---|---|---|---|---|---|---|
| TAGTTAACAA | TGTGGCTGCC | GGGCATATTC | TCCTCAGCTA | GGACCTCAGT | TTTCCCATCT | 4320 |
| GTGAAGACGG | CAGGTTCTAC | CTAGGGGGCT | GCAGGCTGGT | GGTCCGAAGC | CTGGGCATAT | 4380 |
| CTGGAGTAGA | AGGATCACTG | TGGGGCAGGG | CAGGTTCTGT | GTTGCTGTGG | ATGACGTTGA | 4440 |
| CTTTGACCAT | TGCTCGGCAG | AGCCTGCTCT | CGCTGGTTCA | GCCACAGGCC | CCACCACTCC | 4500 |
| CTATTGTCTC | AGCCCGGGT | ATGAAACATG | TATTCCTCAC | TGGCCTATCA | CCTGAAGCCT | 4560 |
| TTGAATTTGC | AACACCTGCC | AACCCCTCCC | TCAAAAGAGT | TGCCCTCTCA | GATCCTTTTG | 4620 |
| ATGTAAGGTT | TGGTGTTGAG | ACTTATTTCA | CTAAATTCTC | ATACATAAAC | ATCACTTTAT | 4680 |
| GTATGAGGCA | AAATGAGGAC | CAGGGAGATG | AATGACTTGT | CCTGGCTCAT | ACACCTGGAA | 4740 |
| AGTGACAGAG | TCAGATTAGA | TCCCAGGTCT | ATCTGAAGTT | AAAAGAGGTG | TCTTTTCACT | 4800 |
| TCCCACCTCC | TCCATCTACT | TTAAAGCAGC | ACAAACCCCT | GCTTTCAAGG | AGAGATGAGC | 4860 |
| GTCTCTAAAG | CCCCTGACAG | CAAGAGCCCA | GAACTGGGAC | ACCATTAGTG | ACCCAGACGG | 4920 |
| CAGGTAAGCT | GACTGCAGGA | GCATCAGCCT | ATTCTTGTGT | CTGGGACCAC | AGAGCATTGT | 4980 |
| GGGGACAGCC | CCGTCTCTTG | GGAAAAAAC | CCTAAGGGCT | GAGGATCCTT | GTGAGTGTTG | 5040 |
| GGTGGGAACA | GCTCCCAGGA | GGTTTAATCA | CAGCCCCTCC | ATGCTCTCTA | GCTGTTGCCA | 5100 |
| TTGTGCAAGA | TGCATTTCCC | TTCTGTGCAG | CAGTTTCCCT | GGCCACTAAA | TAGTGGGATT | 5160 |
| AGATAGAAGC | CCTCCAAGGG | CTTCCAGCTT | GACATGATTC | TTGATTCTGA | TCTGGCCCGA | 5220 |
| TTCCTGGATA | ATCGTGGGCA | GGCCCATTCC | TCTTCTTGTG | CCTCATTTC | TTCTTTTGTA | 5280 |
| AAACAATGGC | TGTACCATTT | GCATCTTAGG | GTCATTGCAG | ATGTAAGTGT | TGCTGTCCAG | 5340 |
| AGCCTGGGTG | CAGGACCTAG | ATGTAGGATT | CTGGTTCTGC | TACTTCCTCA | GTGACATTGA | 5400 |
| ATAGCTGACC | TAATCTCTCT | GGCTTTGGTT | TCTTCATCTG | TAAAAGAAGG | ATATTAGCAT | 5460 |
| TAGCACCTCA | CGGGATTGTT | ACAAGAAAGC | AATGAATTAA | CACATGTGAG | CACGGAGAAC | 5520 |
| AGTGCTTGGC | ATATGGTAAG | CACTACGTAC | ATTTTGCTAT | TCTTCTGATT | CTTTCAGTGT | 5580 |
| TACTGATGTC | GGCAAGTACT | TGGCACAGGC | TGGTTTAATA | ATCCCTAGGC | ACTTCCACGT | 5640 |
| GGTGTCAATC | CCTGATCACT | GGGAGTCATC | ATGTGCCTTG | ACTCGGGGCC | TGGCCCCCCC | 5700 |
| ATCTCTGTCT | TGCAGGACAA | TGCCGTCTTC | TGTCTCGTGG | GGCATCCTCC | TGCTGGCAGG | 5760 |
| CCTGTGCTGC | CTGGTCCCTG | TCTCCCTGGC | TGAGGATCCC | CAGGGAGATG | CTGCCCAGAA | 5820 |
| GACAGATACA | TCCCACCATG | ATCAGGATCA | CCCAACCTTC | AACAAGATCA | CCCCCAACCT | 5880 |
| GGCTGAGTTC | GCCTTCAGCC | TATACCGCCA | GCTGGCACAC | CAGTCCAACA | GCACCAATAT | 5940 |
| CTTCTTCTCC | CCAGTGAGCA | TCGCTACAGC | CTTTGCAATG | CTCTCCCTGG | GACCAAGGC | 6000 |
| TGACACTCAC | GATGAAATCC | TGGAGGGCCT | GAATTTCAAC | CTCACGGAGA | TTCCGGAGGC | 6060 |
| TCAGATCCAT | GAAGGCTTCC | AGGAACTCCT | CCGTACCCTC | AACCAGCCAG | ACAGCCAGCT | 6120 |
| CCAGCTGACC | ACCGGCAATG | GCCTGTTCCT | CAGCGAGGGC | CTGAAGCTAG | TGGATAAGTT | 6180 |
| TTTGGAGGAT | GTTAAAAAGT | TGTACCACTC | AGAAGCCTTC | ACTGTCAACT | TCGGGGACAC | 6240 |
| CGAAGAGGCC | AAGAAACAGA | TCAACGATTA | CGTGGAGAAG | GGTACTCAAG | GGAAAATTGT | 6300 |
| GGATTTGGTC | AAGGAGCTTG | ACAGAGACAC | AGTTTTTGCT | CTGGTGAATT | ACATCTTCTT | 6360 |
| TAAAGGTAAG | GTTGCTCAAC | CAGCCTGAGC | TGTTCCCACA | GAAACAAGCA | AAAATATTCT | 6420 |
| CAAACCATCA | GTTCTTGAAC | TCTCCTTGGC | AATGCATTAT | GGGCCATAGC | AATGCTTTTC | 6480 |
| AGCGTGGATT | CTTCAGTTTT | CTACACACAA | ACACTAAAAT | GTTTTCCATC | ATTGAGTAAT | 6540 |
| TTGAGGAAAT | AATAGATTAA | ACTGTCAAAA | CTACTGACAG | CTCTGCAGAA | CTTTTCAGAG | 6600 |
| CCTTTAATGT | CCTTGTGTAT | ACTGTATATG | TAGAATATAT | AATGCTTAGA | ACTATAGAAC | 6660 |
| AAATTGTAAT | ACACTGCATA | AAGGGATAGT | TTCATGGAAC | ATACTTTACA | CGACTCTAGT | 6720 |

```
GTCCCAGAAT CAGTATCAGT TTTGCAATCT GAAAGACCTG GGTTCAAATC CTGCCTCTAA    6780
CACAATTAGC TTTTGACAAA AACAATGCAT TCTACCTCTT TGAGGTGCTA ATTTCTCATC    6840
TTAGCATGGA CAAAATACCA TTCTTGCTGT CAGGTTTTTT TAGGATTAAA CAAATGACAA    6900
AGACTGTGGG GATGGTGTGT GGCATACAGC AGGTGATGGA CTCTTCTGTA TCTCAGGCTG    6960
CCTTCCTGCC CCTGAGGGGT TAAAATGCCA GGGTCCTGGG GGCCCCAGGG CATTCTAAGC    7020
CAGCTCCCAC TGTCCCAGGA AAACAGCATA GGGGAGGGGA GGTGGGAGGC AAGGCCAGGG    7080
GCTGCTTCCT CCACTCTGAG GCTCCCTTGC TCTTGAGGCA AAGGAGGGCA GTGGAGAGCA    7140
GCCAGGCTGC AGTCAGCACA GCTAAAGTCC TGGCTCTGCT GTGGCCTTAG TGGGGGCCCA    7200
GGTCCCTCTC CAGCCCCAGT CTCCTCCTTC TGTCCAATGA GAAAGCTGGG ATCAGGGGTC    7260
CCTGAGGCCC CTGTCCACTC TGCATGCCTC GATGGTGAAG CTCTGTTGGT ATGGCAGAGG    7320
GGAGGCTGCT CAGGCATCTG CATTTCCCCT GCCAATCTAG AGGATGAGGA AAGCTCTCAG    7380
GAATAGTAAG CAGAATGTTT GCCCTGGATG AATAACTGAG CTGCCAATTA ACAAGGGGCA    7440
GGGAGCCTTA GACAGAAGGT ACCAAATATG CCTGATGCTC AACATTTTA TTTGTAATAT     7500
CCAAGACACC CTCAAATAAA CATATGATTC AATAAAAAT GCACAGCCAC GATGGCATCT     7560
CTTAGCCTGA CATCGCCACG ATGTAGAAAT TCTGCATCTT CCTCTAGTTT TGAATTATCC    7620
CCACACAATC TTTTTCGGCA GCTTGGATGG TCAGTTTCAG CACCTTTTAC AGATGATGAA    7680
GCTGAGCCTC GAGGGATGTG TGTCGTCAAG GGGGCTCAGG GCTTCTCAGG GAGGGGACTC    7740
ATGGTTTCTT TATTCTGCTA CACTCTTCCA AACCTTCACT CACCCCTGGT GATGCCCACC    7800
TTCCCCTCTC TCCAGGCAAA TGGGAGAGAC CCTTTGAAGT CAAGGACACC GAGGAAGAGG    7860
ACTTCCACGT GGACCAGGTG ACCACCGTGA AGGTGCCTAT GATGAAGCGT TTAGGCATGT    7920
TTAACATCCA GCACTGTAAG AAGCTGTCCA GCTGGGTGCT GCTGATGAAA TACCTGGGCA    7980
ATGCCACCGC CATCTTCTTC CTGCCTGATG AGGGAAAACT ACAGCACCTG GAAAATGAAC    8040
TCACCCACGA TATCATCACC AAGTTCCTGG AAAATGAAGA CAGAAGGTGA TTCCCCAACC    8100
TGAGGGTGAC CAAGAAGCTG CCCACACCTC TTAGCCATGT TGGGACTGAG GCCCATCAGG    8160
ACTGGCCAGA GGGCTGAGGA GGGTGAACCC CACATCCCTG GGTCACTGCT ACTCTGTATA    8220
AACTTGGCTT CCAGAATGAG GCCACCACTG AGTTCAGGCA GCGCCATCCA TGCTCCATGA    8280
GGAGGACAGT ACCCAGGGTG AGGAGGTAAA GGTCTCGTCC CTGGGGACTT CCCACTCCAG    8340
TGTGGACACT GTCCCTTCCC AATATCCAGT GCCCAGGGCA GGGACAGCAG CACCACCACA    8400
CGTTCTGGCA GAACCAAAAA GGAACAGATG GGCTTCCTGG CAAAGGCAGC AGTGGAGTGT    8460
GGAGTTCAAG GGTAGAATGT CCCTGGGGGG ACGGGGAAG AGCCTGTGTG GCAAGGCCCA    8520
GAAAAGCAAG GTTCGGAATT GGAACAGCCA GGCCATGTTC GCAGAAGGCT TGCGTTTCTC    8580
TGTCACTTTA TCGGTGCTGT TAGATTGGGT GTCCTGTAGT AAGTGATACT TAAACATGAG    8640
CCACACATTA GTGTATGTGT GTGCATTCGT GATTATGCCC ATGCCCTGCT GATCTAGTTC    8700
GTTTTGTACA CTGTAAAACC AAGATGAAAA TACAAAAGGT GTCGGGTTCA TAATAGGAAT    8760
CGAGGCTGGA ATTTCTCTGT TCCATGCCAG CACCTCCTGA GGTCTCTGCT CCAGGGGTTG    8820
AGAAAGAACA AAGAGGCTGA GAGGGTAACG GATCAGAGAG CCCAGAGCCA AGCTGCCCGC    8880
TCACACCAGA CCCTGCTCAG GGTGGCATTG TCTCCCCATG GAAAACCAGA GAGGAGCACT    8940
CAGCCTGGTG TGGTCACTCT TCTCTTATCC ACTAAACGGT TGTCACTGGG CACTGCCACC    9000
AGCCCCGTGT TTCTCTGGGT GTAGGGCCCT GGGGATGTTA CAGGCTGGGG GCCAGGTGAC    9060
CCAACACTAC AGGGCAAGAT GAGACAGGCT TCCAGGACAC CTAGAATATC AGAGGAGGTG    9120
GCATTTCAAG CTTTTGTGAT TCATTCGATG TTAACATTCT TTGACTCAAT GTAGAAGAGC    9180
```

| | | | | | | |
|---|---|---|---|---|---|---|
| TAAAAGTAGA | ACAAACCAAA | GCCGAGTTCC | CATCTTAGTG | TGGGTGGAGG | ACACAGGAGT | 9240 |
| AAGTGGCAGA | AATAATCAGA | AAAGAAAACA | CTTGCACTGT | GGTGGGTCCC | AGAAGAACAA | 9300 |
| GAGGAATGCT | GTGCCATGCC | TTGAATTTCT | TTTCTGCACG | ACAGGTCTGC | CAGCTTACAT | 9360 |
| TTACCCAAAC | TGTCCATTAC | TGGAACCTAT | GATCTGAAGA | GCGTCCTGGG | TCAACTGGGC | 9420 |
| ATCACTAAGG | TCTTCAGCAA | TGGGGCTGAC | CTCTCCGGGG | TCACAGAGGA | GGCACCCCTG | 9480 |
| AAGCTCTCCA | AGGTGAGATC | ACCCTGACGA | CCTTGTTGCA | CCCTGGTATC | TGTAGGGAAG | 9540 |
| AATGTGTGGG | GGCTGCAGCT | CTGTCCTGAG | GCTGAGGAAG | GGGCCGAGGG | AAACAAATGA | 9600 |
| AGACCCAGGC | TGAGCTCCTG | AAGATGCCCG | TGATTCACTG | ACACGGGACG | TGGTCAAACA | 9660 |
| GCAAAGCCAG | GCAGGGGACT | GCTGTGCAGC | TGGCACTTTC | GGGGCCTCCC | TTGAGGTTGT | 9720 |
| GTCACTGACC | CTGAATTTCA | ACTTTGCCCA | AGACCTTCTA | GACATTGGGC | CTTGATTTAT | 9780 |
| CCATACTGAC | ACAGAAGGT | TTGGGCTAAG | TTGTTTCAAA | GGAATTTCTG | ACTCCTTCGA | 9840 |
| TCTGTGAGAT | TTGGTGTCTG | AATTAATGAA | TGATTTCAGC | TAAAGATGAC | ACTTATTTTG | 9900 |
| GAAAACTAAA | GGCGACCAAT | GAACAACTGC | AGTTCCATGA | ATGGCTGCAT | TATCTTGGGG | 9960 |
| TCTGGGCACT | GTGAAGGTCA | CTGCCAGGGT | CCGTGTCCTC | AAGGAGCTTC | AAGCCGTGTA | 10020 |
| CTAGAAAGGA | GAGAGCCCTG | GAGGCAGACG | TGGAGTGACG | ATGCTCTTCC | CTGTTCTGAG | 10080 |
| TTGTGGGTGC | ACCTGAGCAG | GGGGAGAGGC | GCTTGTCAGG | AAGATGGACA | GAGGGGAGCC | 10140 |
| AGCCCCATCA | GCCAAAGCCT | TGAGGAGGAG | CAAGGCCTAT | GTGACAGGGA | GGGAGAGGAT | 10200 |
| GTGCAGGGCC | AGGGCCGTCC | AGGGGGAGTG | AGCGCTTCCT | GGGAGGTGTC | CACGTGAGCC | 10260 |
| TTGCTCGAGG | CCTGGGATCA | GCCTTACAAC | GTGTCTCTGC | TTCTCTCCCC | TCCAGGCCGT | 10320 |
| GCATAAGGCT | GTGCTGACCA | TCGACGAGAA | AGGGACTGAA | GCTGCTGGGG | CCATGTTTTT | 10380 |
| AGAGGCCATA | CCCATGTCTA | TCCCCCCCGA | GGTCAAGTTC | AACAAACCCT | TTGTCTTCTT | 10440 |
| AATGATTGAA | CAAAATACCA | AGTCTCCCCT | CTTCATGGGA | AAAGTGGTGA | ATCCCACCCA | 10500 |
| AAAATAACTG | CCTCTCGCTC | CTCAACCCCT | CCCCTCCATC | CCTGGCCCCC | TCCCTGGATG | 10560 |
| ACATTAAAGA | AGGGTTGAGC | TGGTCCCTGC | CTGCATGTGA | CTGTAAATCC | CTCCCATGTT | 10620 |
| TTCTCTG | | | | | | 10627 |

What we claim is:

1. An isolated DNA molecule encoding human $\alpha_1$-antitrypsin, said molecule comprising a set of introns and a set of exons, wherein said set of exons consists of Exons II, III, IV and V of the human $\alpha_1$-antitrypsin gene, and said set of introns consists of Intron II and zero to two additional introns of the human $\alpha_1$-antitrypsin gene.

2. The isolated DNA of claim 1 wherein said Intron II is located between Exons II and III.

3. The isolated DNA molecule of claim 1 wherein said DNA molecule also includes Intron III of the human $\alpha_1$-antitrypsin gene.

4. The isolated DNA molecule of claim 1 wherein said DNA molecule also includes Intron IV of the human $\alpha_1$-antitrypsin gene.

5. The isolated DNA of claim 1 wherein said DNA is in a vector.

6. The isolated DNA of claim 5 wherein said vector is an expression vector.

7. The isolated DNA of claim 6 wherein said vector is pPI.

8. The isolated DNA of claim 6 wherein said vector is a viral vector.

* * * * *